(12) United States Patent
McAuley et al.

(10) Patent No.: US 9,138,555 B2
(45) Date of Patent: *Sep. 22, 2015

(54) BREATHING ASSISTANCE APPARATUS

(75) Inventors: Alastair Edwin McAuley, Auckland (NZ); Oliver Gleeson, Auckland (NZ); Evan Stuart Erstich, Auckland (NZ); Simon Eric Freeman, Auckland (NZ); Neil Glen Davies, Auckland (NZ); Stephen John Schoenberg, Auckland (NZ); Kamman Law, Auckland (NZ); Craig Robert Prentice, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1573 days.

This patent is subject to a terminal disclaimer.

(21) Appl. No.: 12/633,135

(22) Filed: Dec. 8, 2009

(65) Prior Publication Data
US 2010/0083961 A1 Apr. 8, 2010

Related U.S. Application Data

(63) Continuation of application No. 12/307,993, filed as application No. PCT/NZ2007/000185 on Jul. 13, 2007, now Pat. No. 8,443,807.

(30) Foreign Application Priority Data

Jul. 14, 2006 (NZ) ........................................ 548575
Nov. 6, 2006 (NZ) ....................................... 551103

(51) Int. Cl.
*A61M 11/00* (2006.01)
*A61M 16/06* (2006.01)
(Continued)

(52) U.S. Cl.
CPC ........... *A61M 16/0683* (2013.01); *A61M 16/06* (2013.01); *A61M 16/0666* (2013.01);
(Continued)

(58) Field of Classification Search
CPC ................ A61M 16/0666; A61M 2210/0618; A61M 15/08
USPC ............. 128/207.18, 206.21, 206.24, 206.27, 128/207.11, 207.13
See application file for complete search history.

(56) References Cited

U.S. PATENT DOCUMENTS 4,367,735 A 1/1983 Dali
4,753,233 A 6/1988 Grimes
(Continued)

FOREIGN PATENT DOCUMENTS

CN 1784250 A 6/2006
EP 0747078 12/1996
(Continued)

OTHER PUBLICATIONS

English Translation of Chinese Examination Report; 5 pages.
(Continued)

*Primary Examiner* — Steven Douglas
(74) *Attorney, Agent, or Firm* — Knobbe Martens Olson & Bear LLP

(57) ABSTRACT

Headgear for use with a respiratory mask is described. The headgear comprises a continuous and substantially curved elongate member extending in use below a user's nose and at least two headgear straps capable of attachment to the ends of the elongate member. A mask attachment on the elongate member is disposed to sit below or on one of said user's nose, mouth, upper lip and an inlet to the mask. The attachment is capable of receiving the mask.

68 Claims, 21 Drawing Sheets

(51) Int. Cl.
*A61M 16/16* (2006.01)
*A61M 16/08* (2006.01)
*A61M 16/00* (2006.01)

(52) U.S. Cl.
CPC ........... *A61M16/0825* (2014.02); *A61M 16/16* (2013.01); *A61M 16/161* (2014.02); *A61M 16/0611* (2014.02); *A61M 16/0616* (2014.02); *A61M 2016/0039* (2013.01); *A61M 2205/3368* (2013.01); *A61M 2205/3653* (2013.01); *A61M 2205/50* (2013.01); *A61M 2210/0618* (2013.01); *A61M 2210/0625* (2013.01)

(56) References Cited

U.S. PATENT DOCUMENTS

| | | |
|---|---|---|
| 4,782,832 A | 11/1988 | Trimble et al. |
| 4,915,105 A | 4/1990 | Lee |
| 5,042,478 A | 8/1991 | Kopala et al. |
| 5,113,857 A | 5/1992 | Dickerman et al. |
| 5,148,802 A | 9/1992 | Sanders et al. |
| 5,245,995 A | 9/1993 | Sullivan et al. |
| 5,269,296 A | 12/1993 | Landis |
| 5,477,852 A | 12/1995 | Landis et al. |
| 5,533,506 A | 7/1996 | Wood |
| 5,595,174 A | 1/1997 | Gwaltney |
| 5,724,965 A * | 3/1998 | Handke et al. ............ 128/207.13 |
| 5,884,624 A | 3/1999 | Barnett et al. |
| 5,921,239 A | 7/1999 | McCall et al. |
| 6,019,101 A | 2/2000 | Cotner et al. |
| 6,050,260 A * | 4/2000 | Daniell et al. ............ 128/204.22 |
| 6,119,694 A | 9/2000 | Correa et al. |
| 6,298,850 B1 | 10/2001 | Argraves |
| 6,431,172 B1 | 8/2002 | Bordewick |
| 6,439,234 B1 | 8/2002 | Curti et al. |
| 6,478,026 B1 | 11/2002 | Wood |
| 6,561,188 B1 | 5/2003 | Ellis |
| 6,581,594 B1 | 6/2003 | Drew et al. |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,679,257 B1 | 1/2004 | Robertson et al. |
| 6,679,265 B2 | 1/2004 | Strickland et al. |
| 6,907,882 B2 | 6/2005 | Ging et al. |
| 6,951,218 B2 | 10/2005 | Gradon et al. |
| 7,096,864 B1 | 8/2006 | Mayer et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,318,437 B2 | 1/2008 | Gunaratnam et al. |
| 7,896,003 B2 | 3/2011 | Matula et al. |
| 8,443,807 B2 | 5/2013 | McAuley et al. |
| 8,479,741 B2 | 7/2013 | McAuley et al. |
| 2002/0053347 A1 | 5/2002 | Ziaee |
| 2002/0059935 A1 | 5/2002 | Wood |
| 2002/0096178 A1 | 7/2002 | Ziaee |
| 2003/0005933 A1 | 1/2003 | Izuchukwu |
| 2003/0079749 A1 | 5/2003 | Strickland et al. |
| 2003/0172936 A1 | 9/2003 | Wilkie et al. |
| 2003/0200970 A1 | 10/2003 | Stenzler et al. |
| 2004/0226566 A1 | 11/2004 | Gunaratnam et al. |
| 2005/0011524 A1 | 1/2005 | Thomlinson et al. |
| 2005/0028822 A1 | 2/2005 | Sleeper et al. |
| 2005/0076913 A1 | 4/2005 | Ho et al. |
| 2005/0205096 A1 | 9/2005 | Matula et al. |
| 2005/0235999 A1 | 10/2005 | Wood et al. |
| 2006/0060200 A1 | 3/2006 | Ho et al. |
| 2006/0196511 A1 | 9/2006 | Lau et al. |
| 2006/0237018 A1 | 10/2006 | McAuley et al. |
| 2007/0089749 A1 | 4/2007 | Ho et al. |
| 2007/0125385 A1 | 6/2007 | Ho et al. |

FOREIGN PATENT DOCUMENTS

| | | |
|---|---|---|
| FR | 2658725 | 8/1991 |
| FR | 2749176 | 12/1997 |
| WO | WO 98/18514 | 5/1998 |
| WO | WO 99/58181 | 11/1999 |
| WO | 00/74758 | 12/2000 |
| WO | WO 00/74758 | 12/2000 |
| WO | WO 01/41854 | 6/2001 |
| WO | WO 02/074372 | 9/2002 |
| WO | 2004/041341 | 5/2004 |
| WO | WO 2004/041341 | 5/2004 |
| WO | 2004/073778 | 9/2004 |
| WO | WO 2004/073778 | 9/2004 |
| WO | WO 2005/051468 | 6/2005 |
| WO | 2007/041786 | 4/2007 |
| WO | WO 2007/041786 | 4/2007 |

OTHER PUBLICATIONS

Examination Report; Australian Application No. 2007273324; dated May 22, 2012; 3 pages.
International Search Report for International Application No. PCT/NZ2007/000185, dated Oct. 31, 2007, in 4 pages.
Second Chinese Office Action for Chinese Patent Application No. 201210080441.8 dated Dec. 1, 2014 in 11 pages (with English translation).
English Translation of First Office Action for Chinese Application No. 201210080441.8 dated Mar. 24, 2014, in 14 pages.
Australian Examination Report for Patent Application No. 2012265597 dated Dec. 19, 2013, in 5 pages.
Canadian Examination Report for Application No. 2655839 dated Oct. 4, 2013, in 2 pages.

* cited by examiner

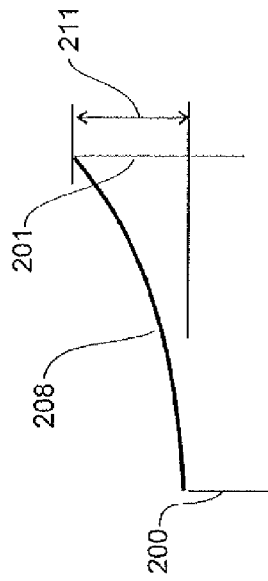
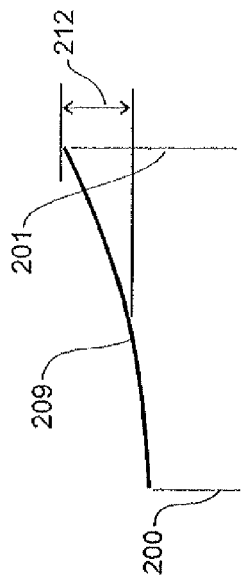
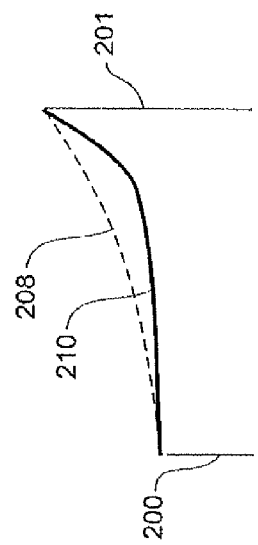
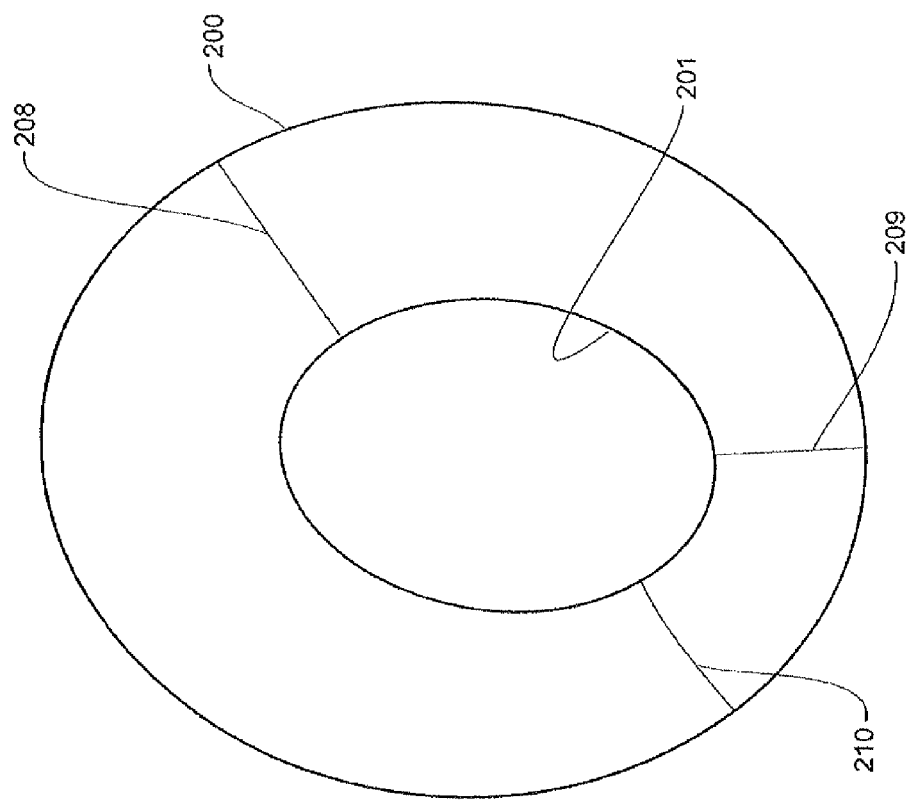

BREATHING ASSISTANCE APPARATUS

This application is a continuation application of U.S. patent application Ser. No. 12/307,993 filed on Jan. 8, 2009 (which accorded a filing date of Jun. 17, 2009 under 35 U.S.C. §371), which is a 371 filing of PCT/NZ2007/000185 filed on Jul. 13, 2007 and published in English as WO 2008/007985 on Jan. 17, 2008. Both applications claim priority from New Zealand Application No. 548575 filed on Jul. 14, 2006 and New Zealand Application No. 551103 filed on Nov. 6, 2006. All of these applications are hereby incorporated by reference in their entirety.

BACKGROUND OF THE INVENTION

1. Technical Field

The present invention relates to apparatus for treating sleep apnoea. More specifically, the present invention provides a nasal interface for the supply of respiratory gases, but most particularly positive pressure gases.

2. Summary of the Prior Art

In the art of respiration devices, a variety of respiratory masks which cover the nose and/or mouth of a human user in order to provide a continuous seal around the nasal and/or oral areas of the face are well known. Masks that provide gas at positive pressure within the mask for consumption by the user are also well known. The uses for such masks range from high altitude breathing (i.e., aviation applications) to mining and fire fighting applications, to various medical diagnostic and therapeutic applications.

Obstructive Sleep Apnoea (OSA) is a sleep disorder that affects up to at least 5% of the population in which muscles that normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a nasal mask. The pressurised air supplied to the patient effectively assists the muscles to keep the patient's airway open, eliminating the typical OSA sleep pattern.

The procedure for administering CPAP treatment has been well documented in both the technical and patent literature. Briefly stated, CPAP treatment acts as a pneumatic splint of the airway by the provision of a positive pressure, usually in the range 4 to 20 cm $H_2O$. The air is supplied to the airway by a motor driven blower whose outlet passes via an air delivery hose to a nose, full face, nose and mouth, or oral mask that is sealingly engaged to a patient's face, preferably by means of a harness or other headgear. An exhaust port is usually also provided in the delivery tube proximate to the mask or on the mask itself. More sophisticated forms of positive airway pressure devices, such as bi-level devices and auto-titrating devices, are described in U.S. Pat. No. 5,148,802 of Respironics, Inc. and U.S. Pat. No. 5,245,995 of Rescare Limited, respectively.

One requisite of respiratory masks has been that they provide an effective seal against the user's face to prevent leakage of the gas being supplied. Commonly, in prior mask configurations, a good mask-to-face seal has been attained in many instances only with considerable discomfort for the user. A common complaint of a user of CPAP therapy is pressure sores caused by the mask about the nose and face and in particular in the nasal bridge region of the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,477,852 of Airways Ltd, Inc. discloses a nasal positive airway pressure device that has a pair of nasal members each having a cannula tip to be inserted into the nares of the patient. Each cannula is tapered from a substantially circular cross section outside the patient's nostril to a substantially oval cross section at the tip inserted into the nostril. An inflatable cuff surrounds each cannula with the interior space of the cuff communicating with the lumen of the cannula through at least one aperture in the sidewall of the cannula. The nasal members are connected to one or more flexible hoses that; in turn, are connected to a source of positive air pressure. In use, positive air pressure is supplied to each cannula tip through the air hoses and nasal members. The positive air pressure inflates the cuffs to hold the nasal members in place and to effect treatment. The nasal device of U.S. Pat. No. 5,477,852 is attached to headgear that is located about a patient's head. This headgear could be considered by many patients as cumbersome and uncomfortable.

Conventional nasal masks used for administrating CPAP treatment are also considered uncomfortable and cumbersome, and prior art nasal masks can be noisy due to air leaks. These disadvantages in many cases are a formidable obstacle to patient acceptance of such treatment. Therefore, a substantial number of patients either cannot tolerate treatment or choose to forego treatment. It is believed a number of such patients might benefit from a nasal positive airway pressure apparatus that is more convenient to use and comfortable to wear, thereby resulting in increased treatment compliance.

Innomed Technologies, Inc. manufactures a nasal cannula device called the NASALAIRE™. In this device air or oxygen travels down a wide bore conduit to nasal cannula. The NASALAIRE™ creates a physical seal between the flares and itself, and relies on the absence of leaks around the cannula and the nares to deliver pressure supplied by a continuous positive airway pressure (CPAP) blower to the airway of the wearer.

U.S. Pat. No. 6,119,694 of Respironics Ga., Inc discloses a nasal mask having a nare seal and lateral support members to support the mask.

WO2004/073778 of ResMed Limited discloses a nasal mask including a frame where headgear is provided with rigid sections that extend to the nasal mask.

WO04/041341 of ResMed Limited discloses headgear for a patient mask that includes a sewn on rigid section to the back area of headgear straps to provide rigidity to the straps.

U.S. Pat. No. 6,907,882 of ResMed Limited discloses a nasal mask and headgear that is attachable to the frame of the nasal mask. The headgear straps have rigid sections integral with the releasable connectors that attach the headgear to the mask.

DISCLOSURE OF THE INVENTION

It is an object of the present invention to attempt to provide a patient interface that goes some way to overcoming the abovementioned disadvantages in the prior art or which will at least provide the industry with a useful choice.

In a first aspect the present invention consists in headgear for use with a respiratory mask comprising:

a continuous and substantially curved elongate member extending in use below a patient's nose, at least two headgear straps capable of attachment to the ends of said elongate member, and a mask attachment on said elongate member disposed to sit below or on one of said user's nose, mouth, upper lip and an inlet to the mask, said attachment capable of receiving said mask.

In a second aspect the present invention consists in a breathing assistance apparatus for use with delivery of respiratory gases to a user comprising:

a mask having a base and body, said body having two flexible nasal pillows that in use rest in a substantially sealed manner against said user's nares, a continuous and substantially curved elongate member extending in use below a patient's nose, at least two headgear straps capable of attachment to the ends of said elongate member, and a mask attachment on said elongate member disposed below said user's nose, said attachment capable of receiving said mask.

In a third aspect the present invention consists in a breathing assistance apparatus for use with delivery of respiratory gases to a user comprising:

a mask comprising a body and a cushion, said cushion substantially forming a seal with said patient's airways, headgear comprising substantially flexible, soft straps and a substantially continuous curved elongate member to which said mask is attached, said elongate member extending over said user's cheeks, and wherein said mask has an inlet extension tube and said curved elongate member is attached or rests beneath said inlet extension tube, anchoring said mask to said user's face in use.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples.

BRIEF DESCRIPTION OF THE FIGURES

Preferred forms of the present invention will now be described with reference to the accompanying drawings.

FIG. 19*a* is a front view of the nasal pillows of FIG. 6.

FIGS. 19*b* to 19*d* are graphs of the gradients of various nasal pillow connecting surfaces.

DESCRIPTION OF THE PREFERRED EMBODIMENTS OF THE INVENTION

The breathing assistance apparatus of the present invention including masks and headgear as described in the preferred embodiments of this invention can be used in respiratory care generally or with a ventilator. It is described below with reference to use in a humidified CPAP system.

Figure 1:
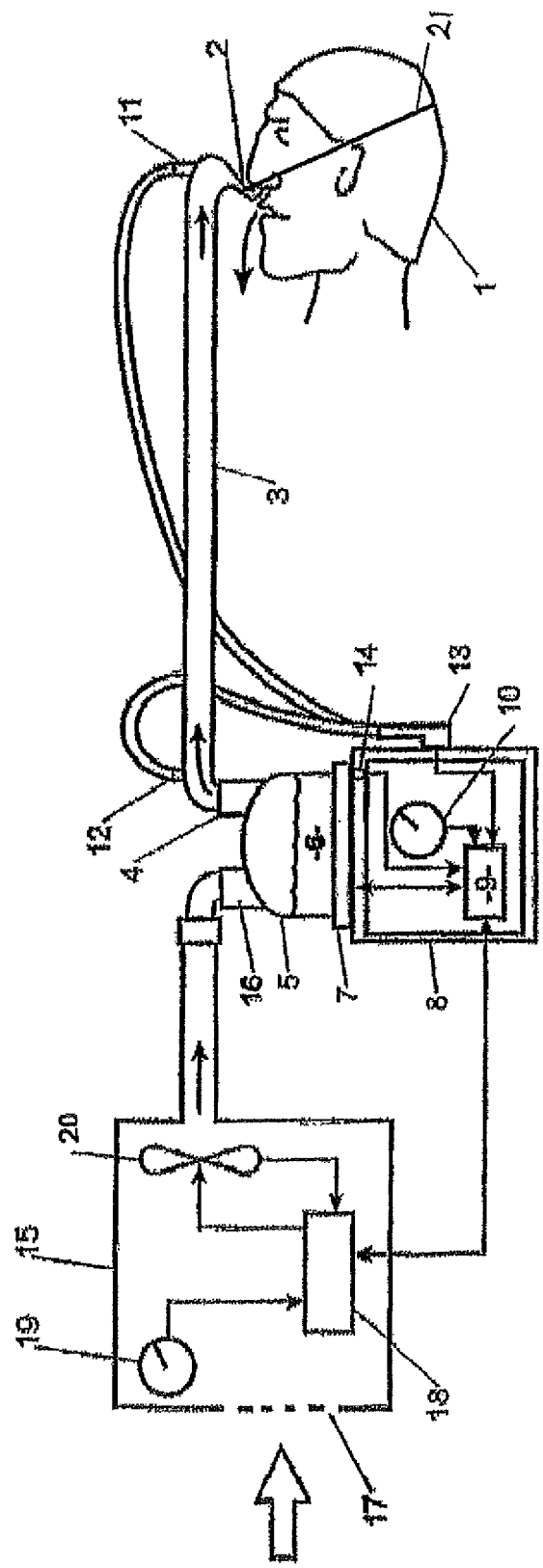
FIG. 1 is a block diagram of a humidified continuous positive airway pressure system as might be used in conjunction with the nasal mask of the present invention.
Figure 7:
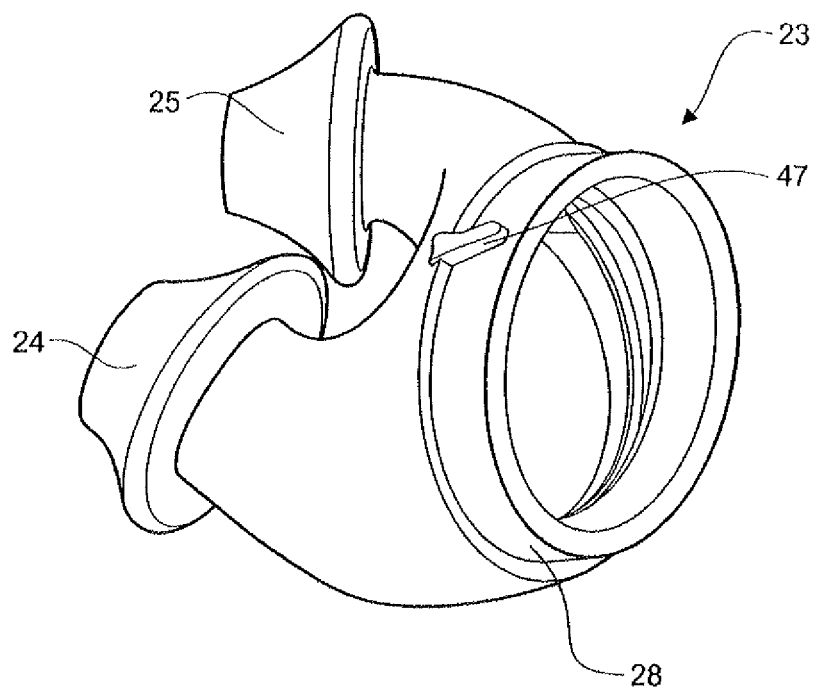
FIG. 7 is a perspective view of the body of FIG. 6.

A humidified Continuous Positive Airway Pressure (CPAP) system is shown in FIG. 1. A patient 1 is receiving humidified and pressurised gases through a patient interface 2 connected to a humidified gases transportation pathway or inspiratory conduit 3. Alternative delivery systems may also be used such as, VPAP (Variable Positive Airway Pressure) and BiPAP (Bi-level Positive Airway Pressure) or numerous other forms of respiratory therapy. A nasal mask 2 is illustrated in FIG. 7 but other masks such as oral, full face or nasal cannula may be used.

An inspiratory conduit 3 is connected to an outlet 4 of a humidification chamber 5 that contains a volume of water 6. The inspiratory conduit 3 may contain heating means or heater wires (not shown) that heat the walls of the conduit to reduce condensation of humidified gases within the conduit 3.

The humidification chamber 5 is preferably formed from a plastics material and preferably has a highly heat conductive base (for example an aluminium base) that is in direct contact with a heater plate 7 of humidifier 8. The humidifier 8 is provided with control means or an electronic controller 9 that may comprise a microprocessor based controller executing computer software commands stored in associated memory.

The controller 9 preferably receives input from sources such as user input means or a dial 10 through which a user of the device may, for example, set a predetermined required value (preset value) of humidity or temperature of the gases supplied to patient 1. The controller 9 may also receive input from other sources, for example temperature and/or flow velocity sensors 11, 12, through a connector 13 and a heater plate temperature sensor 14. In response to the user set humidity or temperature value input via the dial 10 and the other inputs, the controller 9 determines when (or to what level) to energise the heater plate 7 to heat the water 6 within the humidification chamber 5. As the volume of the water 6 within the humidification chamber 5 is heated, water vapour begins to fill the volume of the chamber above the water's surface and is passed out of the humidification chamber 5 outlet 4 with the flow of gases (for example air) provided from a gases supply means or blower 15 that enters the chamber 5 through an inlet 16. Exhaled gases from the patient's mouth are passed directly to the ambient surroundings in FIG. 1.

The blower 15 is provided with variable pressure regulating means or variable speed fan 21 that draws air or other gases through a blower inlet 17. The speed of the variable speed fan 21 is controlled by an electronic controller 18 (or alternatively the function of the controller 18 may be carried out by the controller 9) in response to inputs from the controller 9 and a user set predetermined required value (preset value) of pressure or the fan speed via dial 19.

Figure 2:
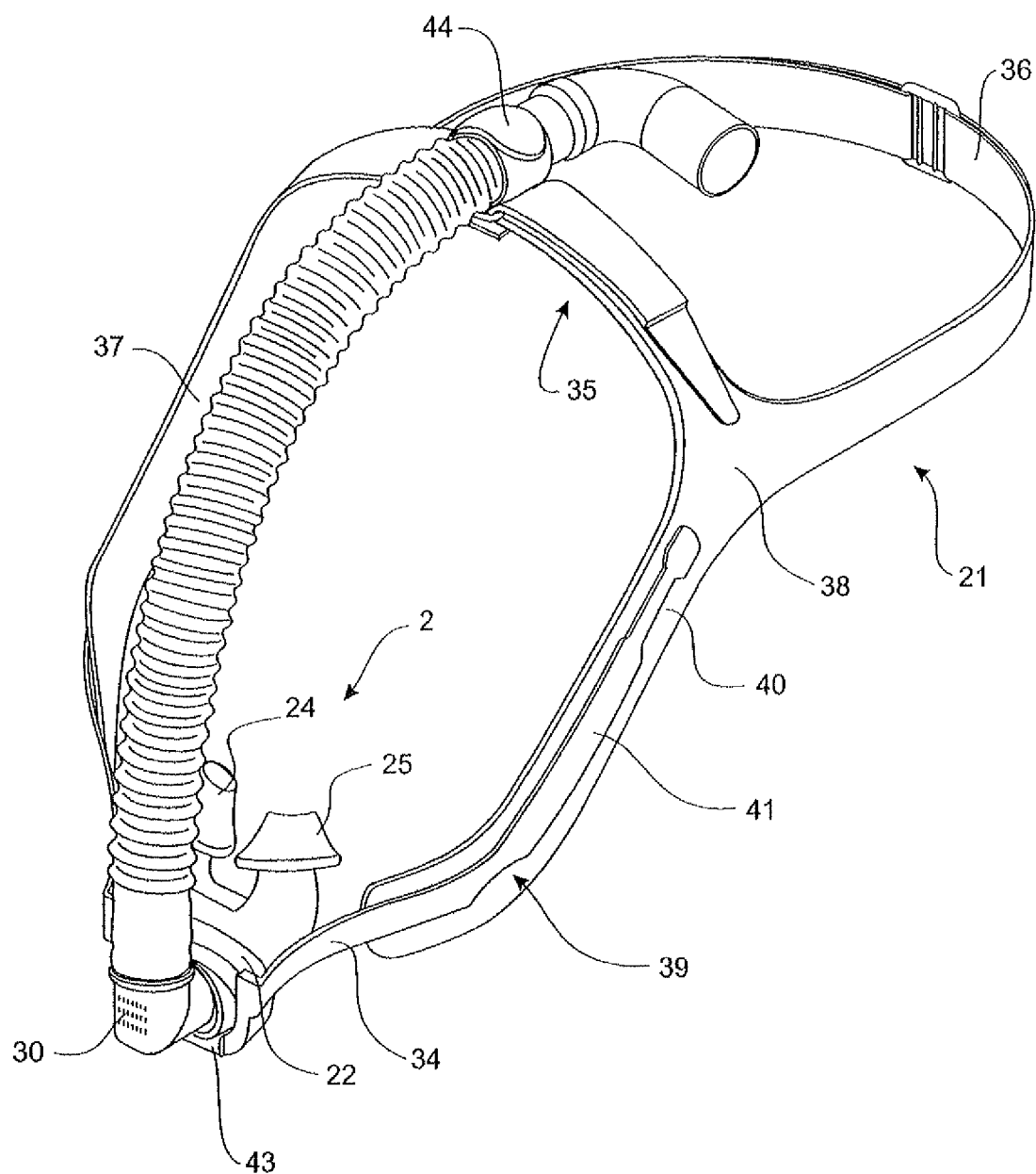
FIG. 2 is a perspective view of a first form of a patient interface that is nasal mask and headgear of the present invention.
Figure 3:
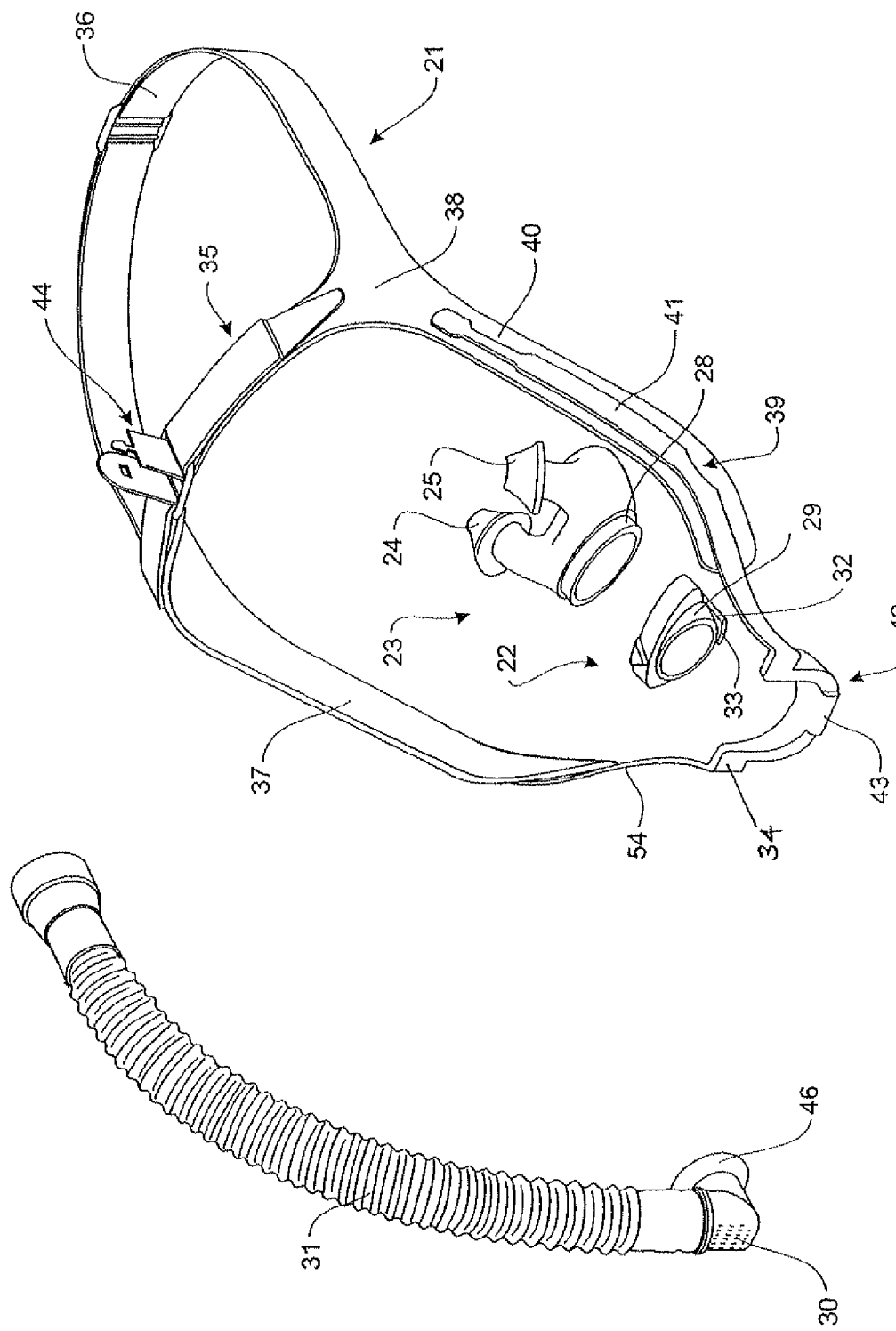
FIG. 3 is an exploded view of the nasal mask and headgear of FIG. 2.

FIGS. 2 and 3 show a first embodiment of a patient interface of the present invention. This patient interface is a nasal mask 2. The nasal mask 2 is comprised of a mask base 22 and body 23. The body 23 is substantially tubular with two nasal pillows 24, extending from it. The nasal pillows 24, 25 are preferably frustoconical in shape and in use rest against a patient's nares, to substantially seal the patient's nares. The body 23 has an external lip 28 that frictionally fits in a channel in the mask base 22.

Figure 6:
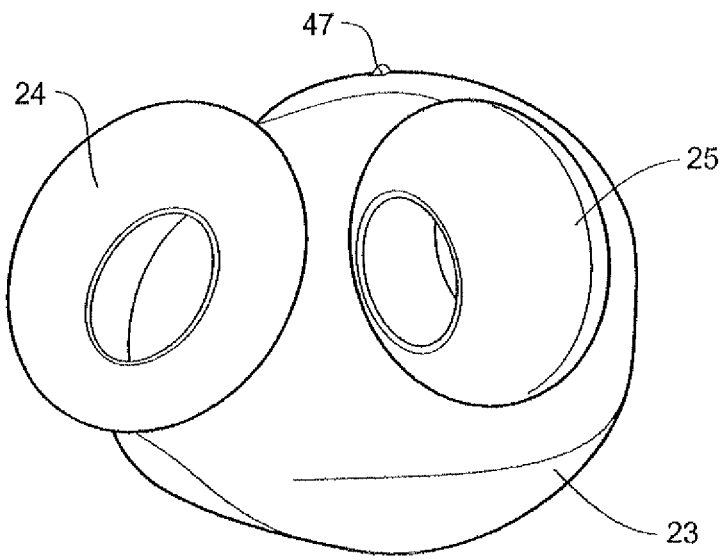
FIG. 6 is an end view of a body of the nasal mask and headgear of FIG. 2, particularly showing two nasal pillows.

The body 23 and nasal pillows 24, 25 of the nasal mask of the present invention are shown in further detail in FIGS. 6 and 7. The body and pillows are preferably integrally moulded in a substantially flexible plastics material. In the preferred form this material is silicone, but other appropriate materials, such as, rubber, thermoset elastomer or thermoplastic elastomer, such as Kraton™ may be used.

The nasal pillows 24, 25 are preferably an elliptical cone and as such are tubular and allow for a passage of gases to flow from the tubing 3 and through the mask body 23. The pillows 24, 25 are preferably angled toward one another and each have a preferably elliptical outlet 26, 27 that may be slightly offset from the centre of each pillow 24, 25, as shown in FIG. 6.

Figure 18:
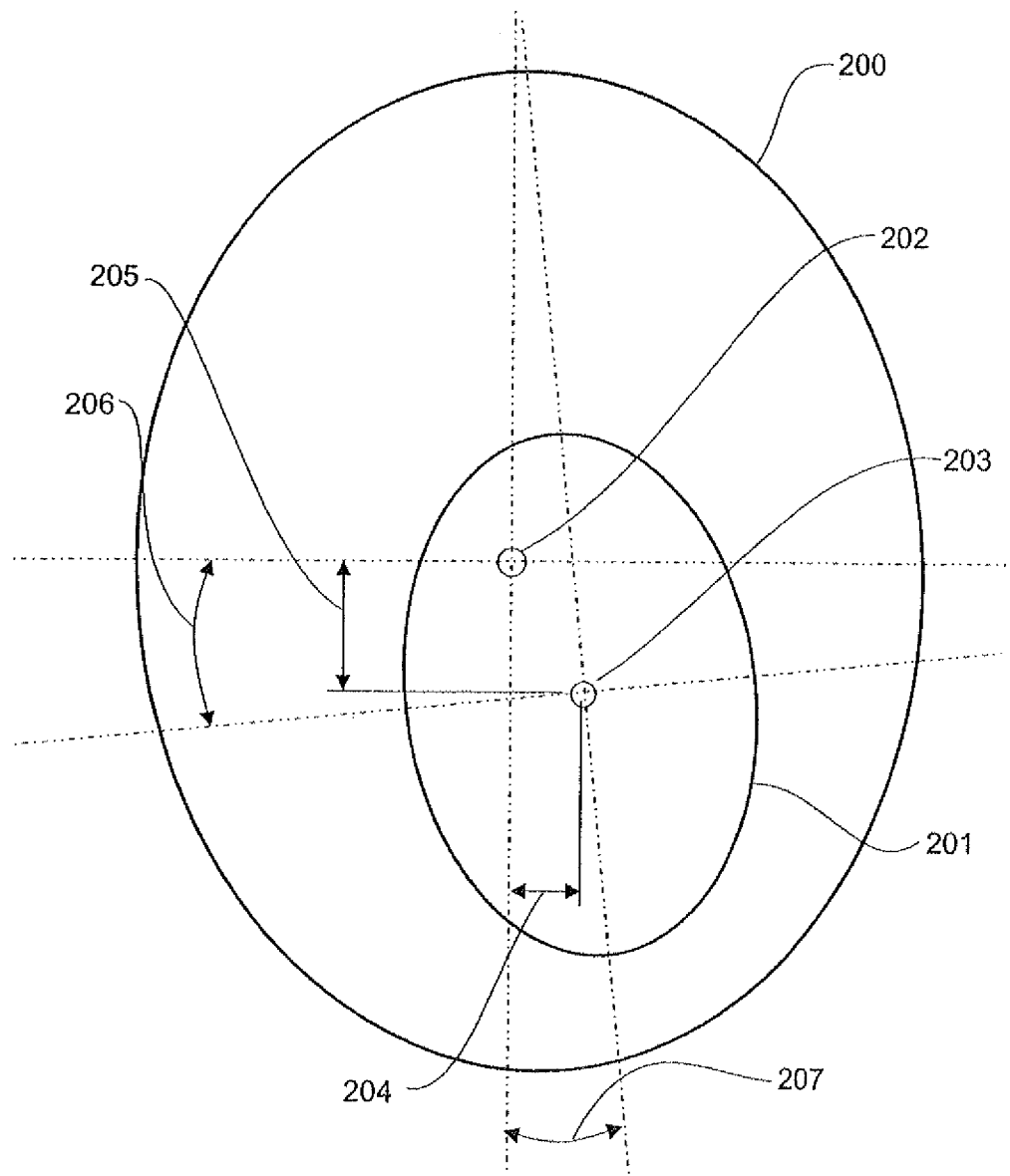
FIG. 18 is a front view of a nasal pillow of FIG. 6.

FIGS. 18 and 19a show a nasal pillow 24 with an offset outlet in more detail. The pillow 24 has an outer profile 200 and inner profile 201 with respective centre points 202, 203. The inner profile 201 (outlet of the nasal pillow 24) is offset inward, by a horizontal spacing 204 and vertical spacing 205. Meaning the outlet 201 of the nasal pillow is offset horizontally 204 towards the middle of the nose and vertically 205 towards the user's upper lip. Offsetting the outlet 201 downwards in this manner allows the outlet to be inserted into a user's nostril without the outer profile 200 pushing the user's upper lip. Offsetting the outlet 201 inwards allows the pillow to better seal on the septum of the user's nose in use.

The outlet 201 may also be angled compared to the outer profile 200. For example in FIG. 18, there is a horizontal angle difference between the outer profile 200 and outlet 201 shown as 206. A similar vertical angle difference between the outer profile 200 and outlet 201 is shown as 207.

With the outer profile and inner profile having different sections or offsets allows the gradient of the connecting surface between the profiles to be changeable. This is shown in the graphs of FIGS. 19b, 19c and 19d. The connecting surface between the inner 201 and outer 200 profiles can have differing gradients, 208, 209, 210. The different gradients 208, 209, 210 of the connecting surface are possible due to the difference in offset difference 211, 212 (horizontal, vertical or angled) between the inner 201 and outer 200 profiles.

There may also be a difference in the rate of change of the gradient (as illustrated in the difference between 208 and 210). This allows easier insertion of the pillow 24 into a user's nostrils due to more lead in and better sealing that may be achieved due to more ergonomic contouring of the connecting surface that contacts the user's nostril.

Referring back to FIG. 7, the external lip 28 on the mask body 23 is an area of reduced circumference around the tubular part of the body 23. A projection 47 may be provided on the lip 28 that fits with a corresponding recess or channel (discussed below) on the mask base 22 to ensure correct assembly of the nasal mask.

Figure 4:
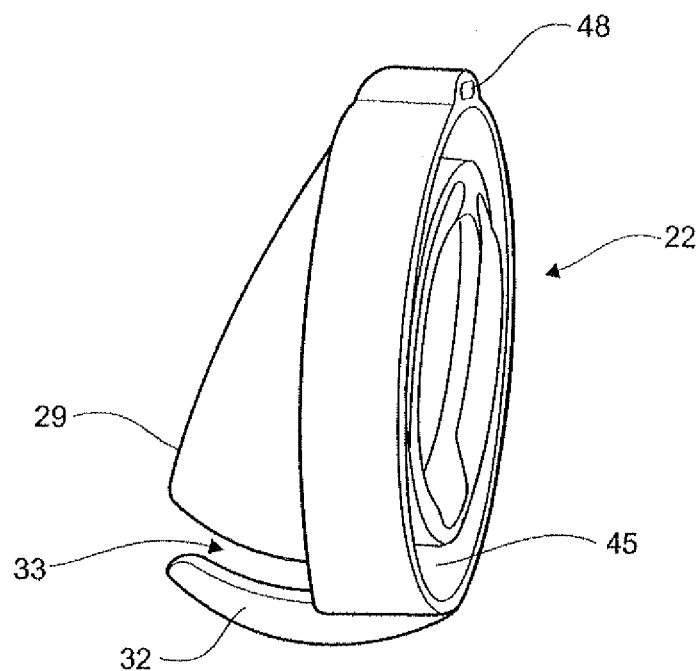
FIG. 4 is a side view of a mask base of the nasal mask and headgear of FIG. 2.
Figure 5:
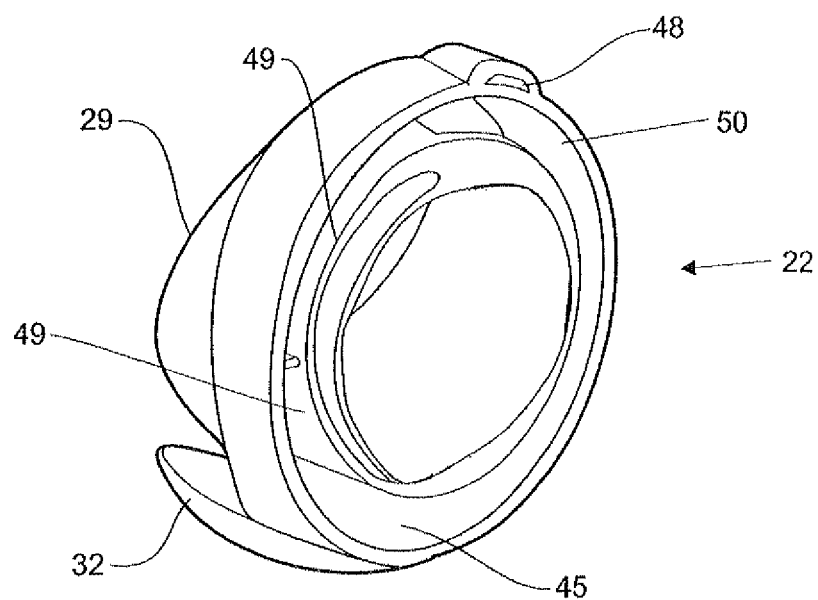
FIG. 5 is a perspective end view of the mask base of FIG. 4.

The mask base 22 is shown in further detail in FIGS. 4 and 5. The mask base 22 is a ring or sleeve type attachment. The base 22 is preferably made from a substantially hard (rigid) plastics material, such as polypropylene, polycarbonate or acetyl. However, other appropriate materials may be used. The base 22 has an internal circumferential recessed area or channel 45 on one side and a semi-tubular projection 29 on its other side. When assembling the mask body 23 to the mask base 22 the channel 45 receives the lip 28. These parts are maintained together by friction fit, however other types of fitting may be provided for, such as a snap or bump fitted part or the body may be over moulded to a clip that causes the fitting to the mask body 23. In this form the friction fitting of the lip 28 to the recessed area 45 is assisted by elongate projections 49 extending along the central part 50 of the mask base 22. The projection 47 on the mask body 23 allows for correct fitting or keying of the mask base to the mask body, such that when the lip 28 is fitted into the recessed area 45, the projection 47 enters the recess 48 formed in the mask base 22.

The semi-tubular projection 29 is curved in this embodiment such that a ball jointed connector end 46 such that a connector 30 can be fitted into it. The projection 29 forms a socket for the connector end 46 and the connector end can swivel within the socket. The connector 30 is attached to a tube 31 to allow for gases to be passed to the nasal mask 2. The tubing 31 may be attached to inspiratory conduit 3 or the tubing 31 may simply be the inspiratory conduit 3.

In alternative embodiments the projection 29 may not be semicircular but the inner surface of the base 22 may be curved and form a socket for receiving the connector end 46.

The base 22 has an extension or partial lip 32 extending beneath the semi-tubular projection (socket) 29. A slot 33 is created between the socket 29 and extension 32. The extension and slot is used to fit the mask base 22 to the headgear 21. In this embodiment the extension 32 is substantially curved to follow the shaped of the projection 29. However, in other forms the extension may be substantially straight or otherwise shaped.

In use, the nasal mask is assembled with headgear 21. The headgear 21 in the preferred form is comprised of headgear straps 35, 36, 37, 38 and a substantially curved and elongate member 34. The member 34 is curved and substantially rigid, or at least more rigid than the headgear straps.

The headgear straps 35, 36, 37, 38 are preferably made from a composite foam layered material, such as Breathoprene™. The headgear 21 preferably includes a first strap 35 and a second strap 36. The first strap 35 extends in use over the forehead or top front area of a patient's head. The second strap 36 extends around the back of the patient's head. The headgear 21 also has side straps 37, 38 that in use extend down the checks of a patient and the ends of the straps terminate in the upper lip area of the patient in use.

Referring to FIG. 2, the curved and elongate member 34 is comprised of a central section 42 and contoured side arms 41, 54. A substantial length of each of the side arms 41, 54 overlaps and is attached to the side straps 37, 38. However, the side straps 37, 38 only extend partially along the length of the side arms 41, 54 so as to terminate beneath the cheek or near the upper lip region. As the side straps 37, 38 are made from a soil foam type material they provide a comfortable fitting of the headgear and curved member 34, while the substantially rigid side arms 41, 54 provide rigidity and stability to the headgear 21 and nasal mask 2. The attachment between the side straps and rigid extension side arms may be made by gluing, sewing or other appropriate fastening.

Preferably the side arms of the curved member 34 are integrally moulded with the central section 42. The curved member 34 is preferably three dimensionally moulded to a shape to substantially match the cheek contours of a human. The side arms 41, 54 are preferably of thinner width (cross-section) than the central section 42. As the side arms 41, 54 are moulded of a plastics material to be substantially thin they are capable of being bent or adjusted to allow for better and more comfortable fit to a patient. The side arms 41, 54 may also include weakened or narrow areas 39 to allow for additional bending, moulding or twisting of the arms 41, 54 to better fit the headgear to individual patients. For example, in the embodiment shown in FIGS. 2 and 3, the narrowed area 39 corresponds to the cheek bone area of a patient and allows for the side arms 41, 54 to easier bend or twist to fit the contours of the patient's face.

In alternative embodiments the side arms may have weakened areas that are narrower in cross-section to that of the remainder of the side arms. A narrower cross-section area would also provide a weakened area that may be easily manipulated.

In alternative embodiments of the present invention the side straps of the headgear may not extend under and along the length of the curved member but be attached to the distal ends of the straps. This attachment may be by hook and loop material, as is known in the art, or by other attachment methods as known in the art. In this form, the arms of the curved member may have padding underneath them or no padding at all.

Referring to FIG. 3, the curved elongate member has a central section 42 that in an assembled form supports the mask base and body such that the pillows 24, 25 rest against the patient's nares. The central section 42 is a half circle that is integrally moulded with the side arms 41, 54. The central section 42 has a raised area 43 on its exterior, at the apex of the half circle. The raised area 43 is shaped to receive the mask base 22. To assemble, a patient merely needs to slide the mask base 22 into the central section 42 such that the raised area 43 fits into the slot 33 on the mask base 22.

The side arms 41, 54 of the curved member 34 preferably have varying cross-sectional thickness. The ends of the arms 41, 54 attached to the central section 42 are thicker over the most curved parts 55, 56 of the arms, whereas the straighter parts of the arms 57, 58 have a narrow cross-section. Therefore, the thicker ends 55, 56 hold their shape better.

In alternative embodiments, the mask base 22 may be formed integrally with the curved member 34. Therefore, the central section and base would be one and would not be able to be separated from one another.

Figure 20:
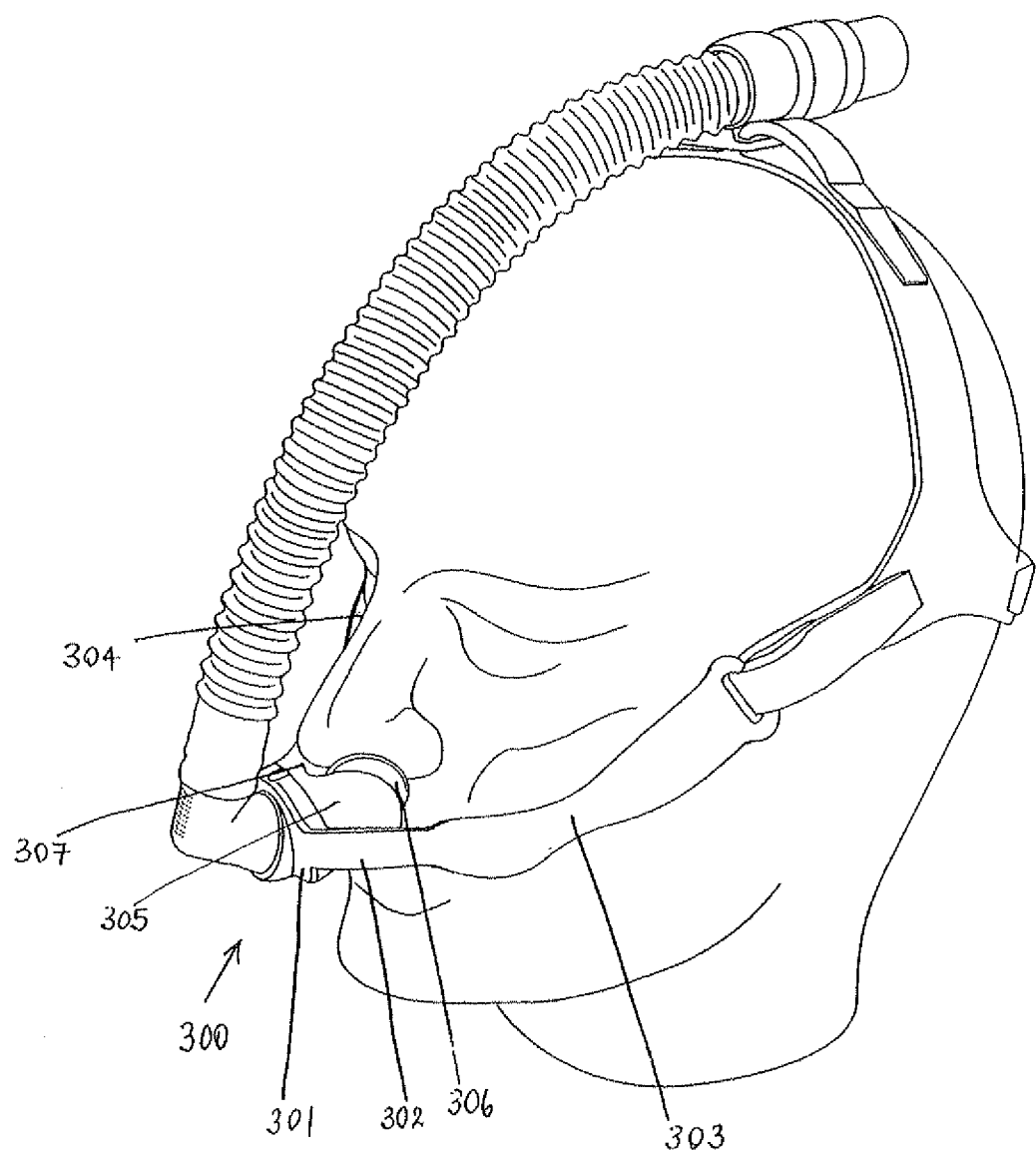
FIG. 20 is a perspective view of an eighth form of a patient interface and headgear of the present invention.
Figure 21:
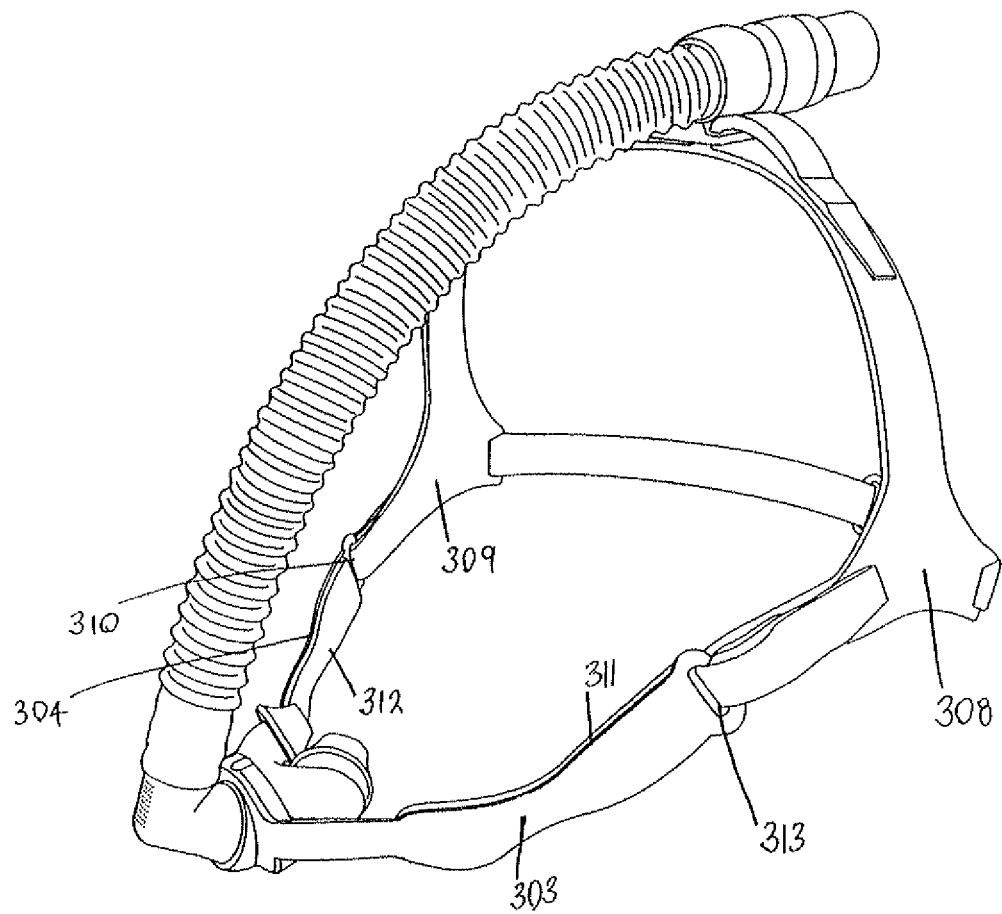
FIG. 21 is a perspective view of the interface and headgear of FIG. 20 showing inner pads on the arms of the headgear.
Figure 22:
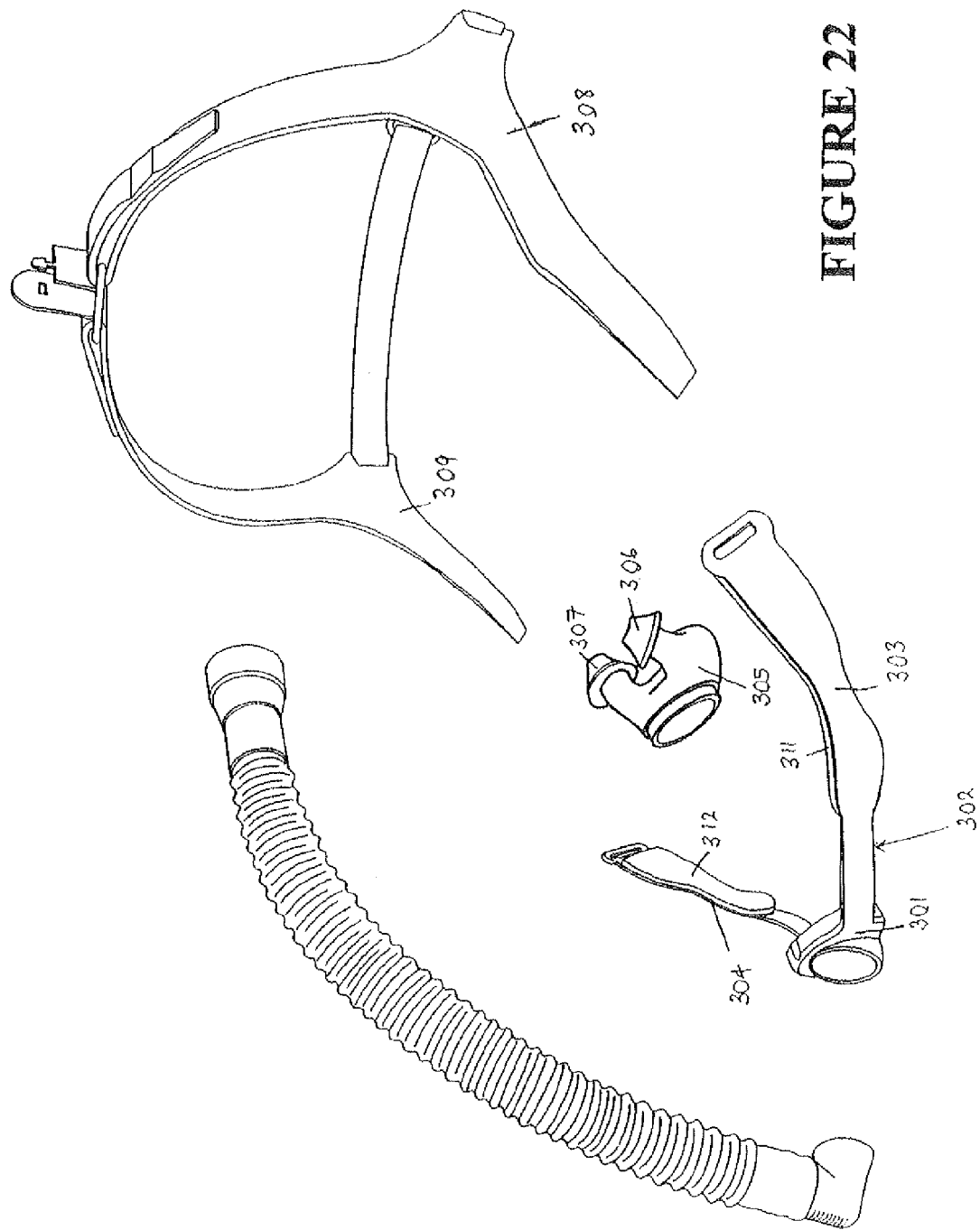
FIG. 22 is an exploded view of the interface and headgear of FIG. 20.

An example of this is shown in FIGS. 20 to 22, the eighth embodiment of the patient interface and headgear 300. Here, the mask base 301 and the curved elongate member 302 are integrally formed, for example, by moulding or the like. The elongate member comprises arms 303, 304 similar to that described above. Also the mask body 305 has integral nasal pillows 306, 307 similar to that described above in relation to FIG. 2.

As can be seen in FIGS. 21 and 22 in this eighth embodiment the headgear straps 308, 309 do not extend down the arms 303, 304 as with other embodiments. In this embodiment the headgear straps 308, 309 attach through recesses 310, 313 at the end of the arms 303, 304 extending along the arms are inner pads 311, 312 that rest against the patient's cheekbones in use and provide comfort to the patient's face. The pads 311, 312 only extend up to near the attachment recesses 309, 310. The pads are preferably made from a foam type material, such as the laminated material that the headgear straps are made from. The pads 311, 312 preferably do not extend beyond the edges of the arms 303, 304.

Referring back to FIGS. 2 and 3, alternatively, the curved member 34 may be formed as two separate pieces. That is, the central section 42 may be formed as two parts with a central split seam, the two left and right halves joined in use. The two left and right parts could either be joined along a seam as described above, with the base 22 slotting into the slot 33 as described above, or alternatively, each of the two left and right arms may be attached one to each side of the base 22.

Where a "substantially continuous elongate member" or "curved member" is referred to in this specification, it refers to any of the options for the curved member 34 outlined above.

The side arms 41, 54 may also include a loop 40 or detached section. This is where a section of the side arms 41 is not attached to the strap 38, 37 lying underneath. Thus the detached section 40 of the side arms forms a loop to which a tubing attachment 44 (such as that shown attached to another strap in FIGS. 2 and 3) may be looped to the side arms 41, 54 and the tubing 31 attached to either of the side arms.

The connector 30 in the preferred form is a ball and socket jointed connector to allow for the tubing 31 to swivel in the mask base 22. The tubing 31 may be attached to any of the headgear straps. However, a tube attachment 44 is shown where the tubing is attached by fasteners, such as hook and loop fastener, to the first strap 35. In other embodiments the tubing 31 may be attached to either the side straps 37, 38 or merely allowed to fall freely from the nasal mask 2.

Although a ball and socket joint, as described above, between the mask base 22 and tubing 31 is preferred other connections may be utilised, such as a flexible piece of silicone, or other appropriate connection. The connection between the base and tubing must be able to be flexed or rotated to allow for the tubing to be moved without causing the dislodgement of the nasal mask 2 from the user's nares.

The mask body 23 may be provided with nasal pillows of various different sizes, such that user's may remove an existing mask body and simply attach a different sized body to the mask base 22.

Figure 8:
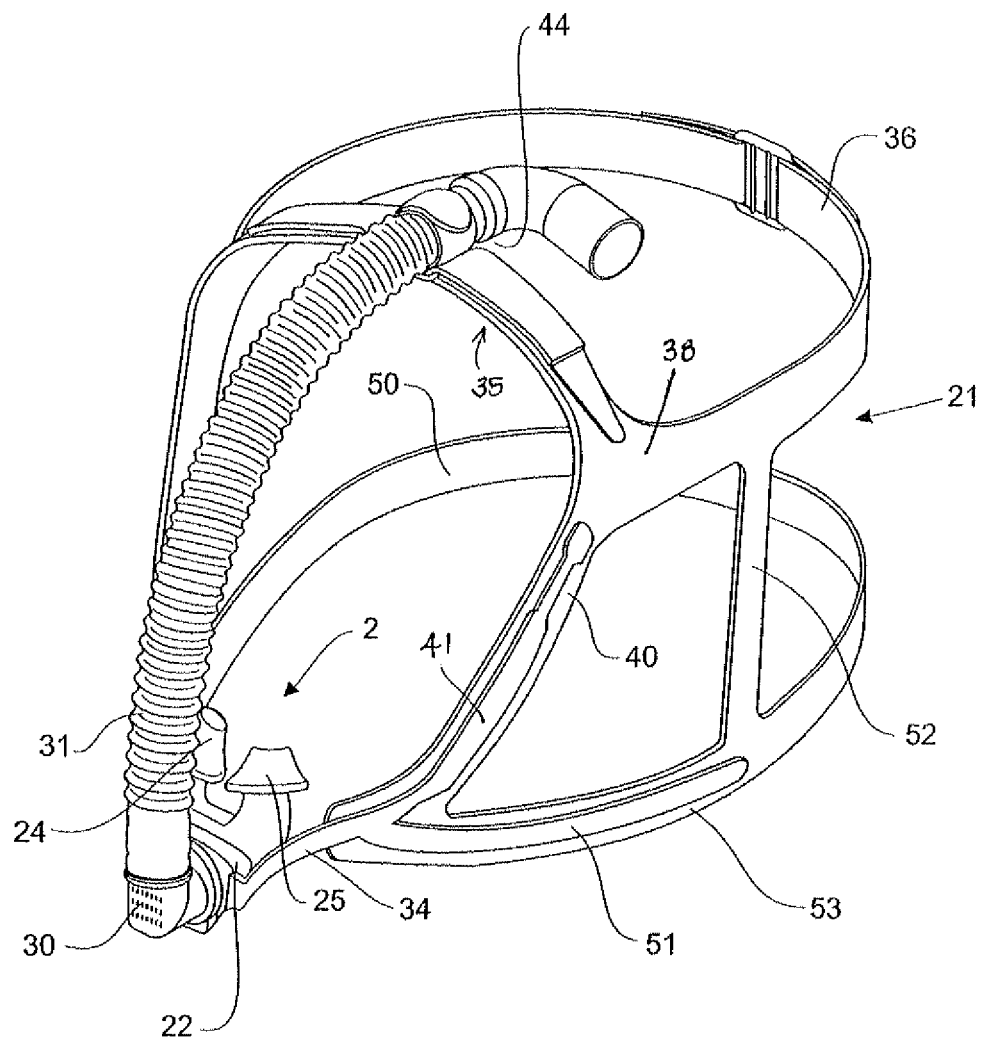
FIG. 8 is a perspective view of a nasal mask of the first form of the present invention but having alternative headgear that includes additional rigid extensions.

Alternative headgear may be used with the patient interface of the present invention. In particular, alternative headgear is shown in use with the first form of the patient interface (of FIG. 2) in FIG. 8. Here the headgear may include an additional strap 53 extending from the cheek region of the side straps 41 and extending behind the user's head. This lower additional strap 53 may also include substantially rigid arms 51 similar to the arms 41 described above. Any number of connecting straps 52 may also be provided between the upper strap 36 and lower strap 53. Again, the arms 51 would provide stability and rigidity to the additional strap 53.

In the embodiment described above, when the patient interface of the first form is in use, the user's face causes the mask base 22 and body 23 to clip with the curved member 34. This is due to the angle of the curved member 34 and fixing of the mask base 22 and body 23 to the curved member 34.

Further, in all forms, the curved member 34 transfers the load of the patient interface away from the user's nose and to the cheek regions of the user.

Figure 9:
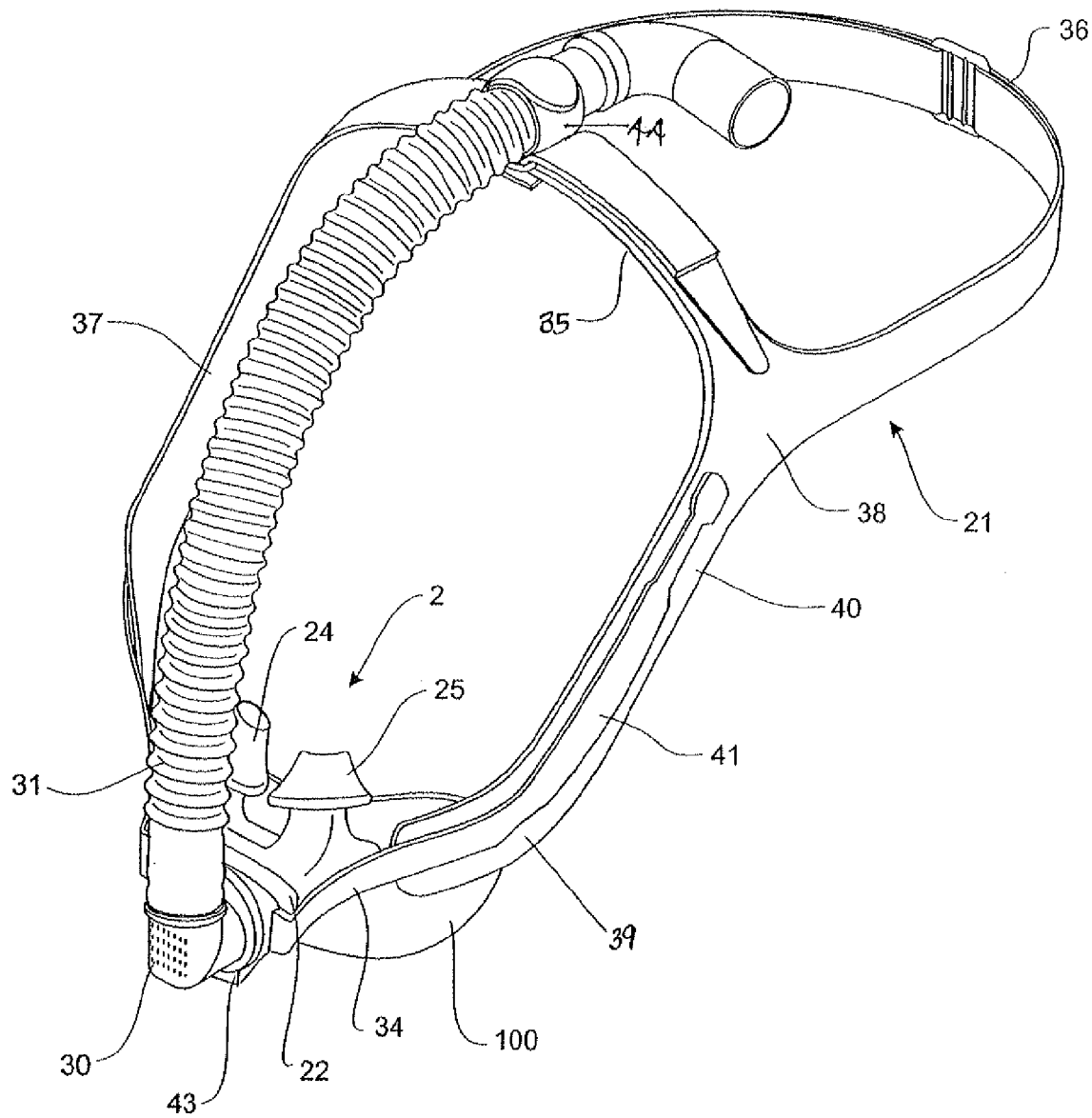
FIG. 9 is perspective view of a second form of a patient interface and headgear of the present invention.
Figure 10:
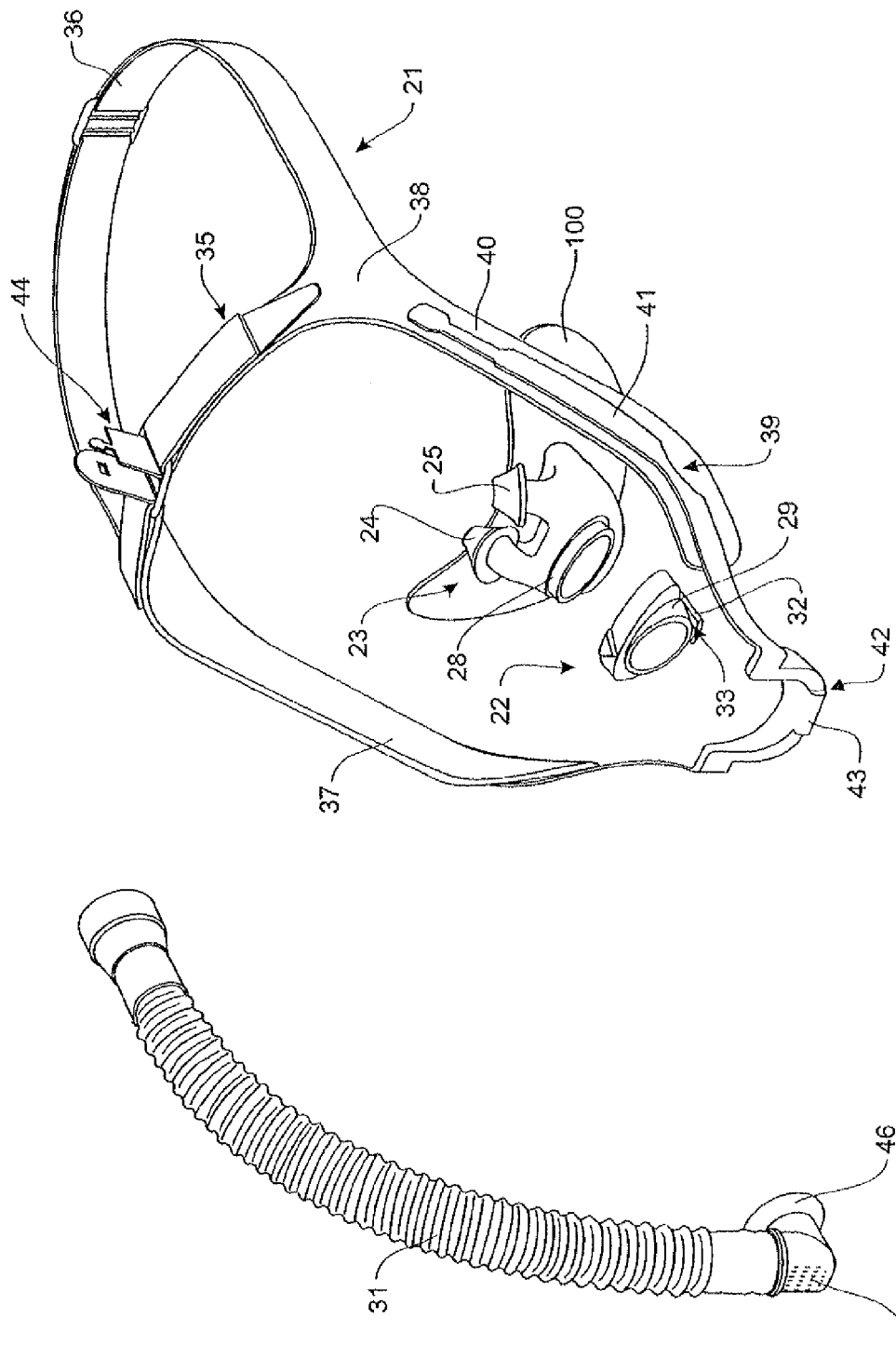
FIG. 10 is an exploded view of the patient interface and headgear of FIG. 9.

A second form of the patient interface and headgear of the present invention is shown in FIGS. 9 and 10. In this embodiment a mouthpiece 100 is attached to the substantially tubular mask body 23 substantially below the nasal pillows 24, 25. The mouthpiece 100 is preferably a flap that is fittable within the patient's mouth. A gases pathway extends through the mask body 23 and through the centre of the mouthpiece 100, such that in use a patient or user is supplied with gases via the nasal pillows 24, 25 and the mouthpiece 100. The flap 100 is preferably made from a silicone plastics material but other appropriate materials such as rubber, thermoset elastomer or thermoplastic elastomer, such as Kraton™ may be used. The flap 100 is preferably integrally moulded with the mask body 23 and nasal pillows 24, 25. In use the flap 100 sits within the user's mouth between the user's teeth and lips.

In this second form the headgear and particularly the curved member 34 is substantially the same as that described in relation to the first embodiment.

Figure 11:
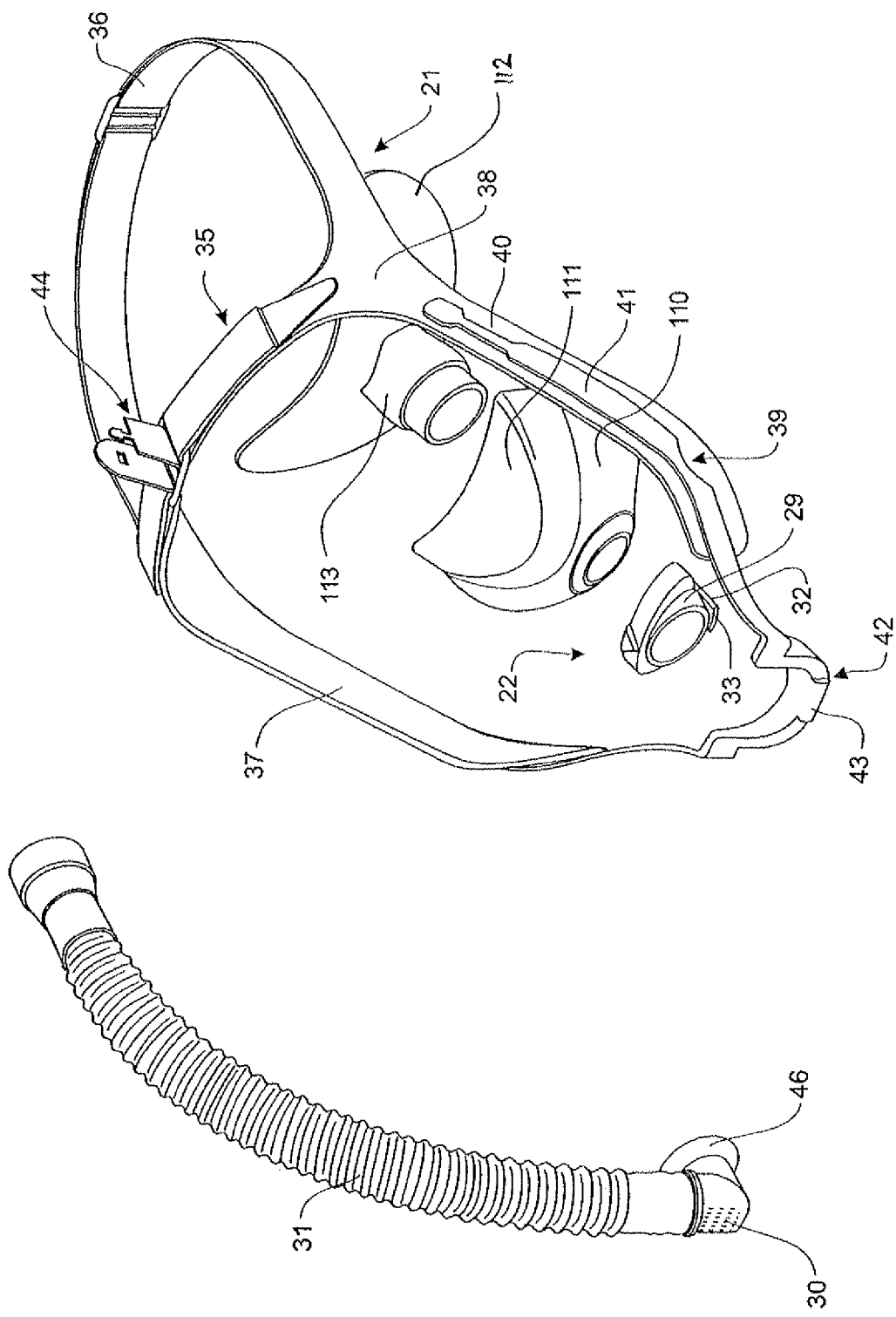
FIG. 11 is an exploded view of a third form of a patient interface and headgear of the present invention.

A third form of the patient interface and headgear of the present invention is shown in FIG. 11. In this embodiment a mouthpiece as well as a nose blocking device is attachable to the mask base 22. The mouthpiece 110 and nose blocking device 111 are preferably integrally formed. The mouthpiece 110 has an inner vestibular shield 112 that is similar to the flap 100 described above. Therefore the vestibular shield 112 in use sits within the patient's mouth between the patient's teeth and lips and provides an at least partial seal between the user and the shield 112.

A tubular extension 113 extends through the mouthpiece 110 to the mask base 22 from the vestibular shield 112. The extension allows for gases to be passed to the patient from the conduit 31.

The nose blocking device 111 in use rests under the user's nose and blocks the user's nares.

In this third form the headgear and particularly the curved member 34 is substantially the same as that described in relation to the first embodiment.

Figure 12:
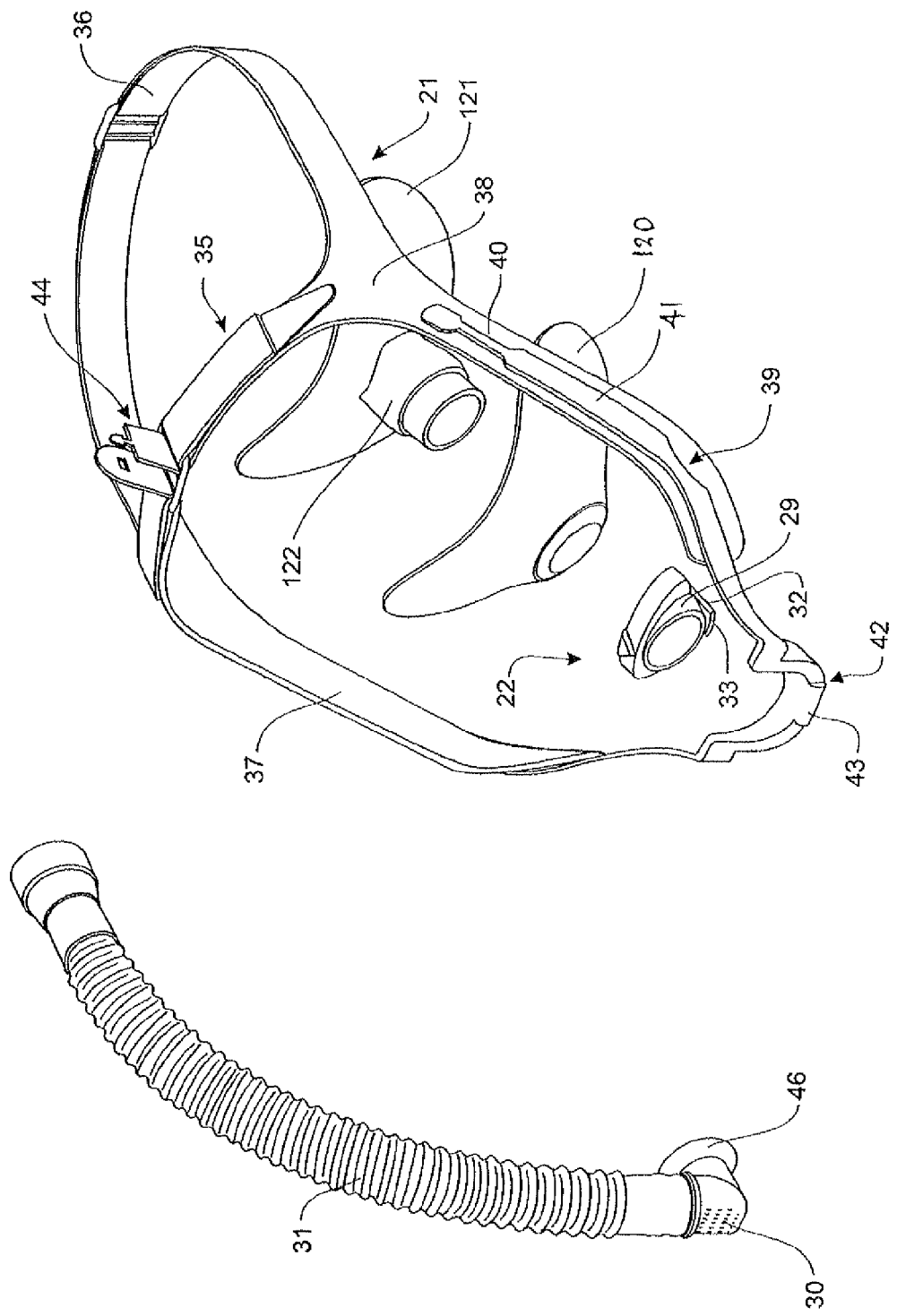
FIG. 12 is an exploded view of a fourth form of a patient interface and headgear of the present invention.

A fourth embodiment of the patient interface and headgear of the present invention is shown in FIG. 12. In this embodiment a mouthpiece 120, 121 is attachable via a tubular extension 122 to the mask base 22. The mouthpiece is made up of an outer mouthpiece flap 120 and an inner vestibular shield 121. The shield 121 is substantially the same as that described in reference to the third embodiment. The outer mouthpiece flap 120 rests in use outside the user's mouth and substantially seals about the user's mouth. The outer mouthpiece flap 120 and an inner vestibular shield 121 are described in further detail in U.S. Pat. No. 6,679,257, the entire contents of which is herein incorporated by reference.

In the fourth form of the headgear and particularly the curved member 34 is substantially the same as that described in relation to the first embodiment.

Figure 13:
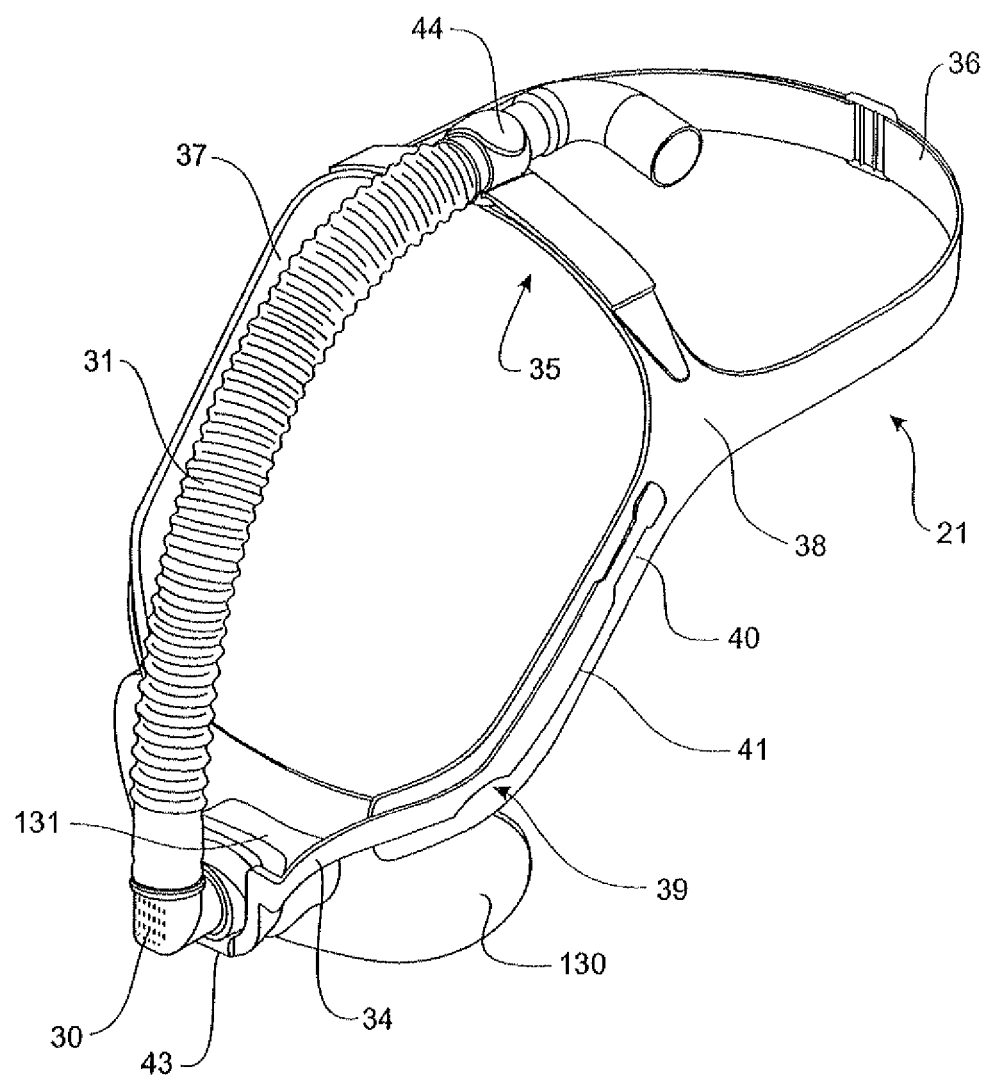
FIG. 13 is a perspective view of a fifth form of a patient interface and headgear of the present invention.
Figure 14:
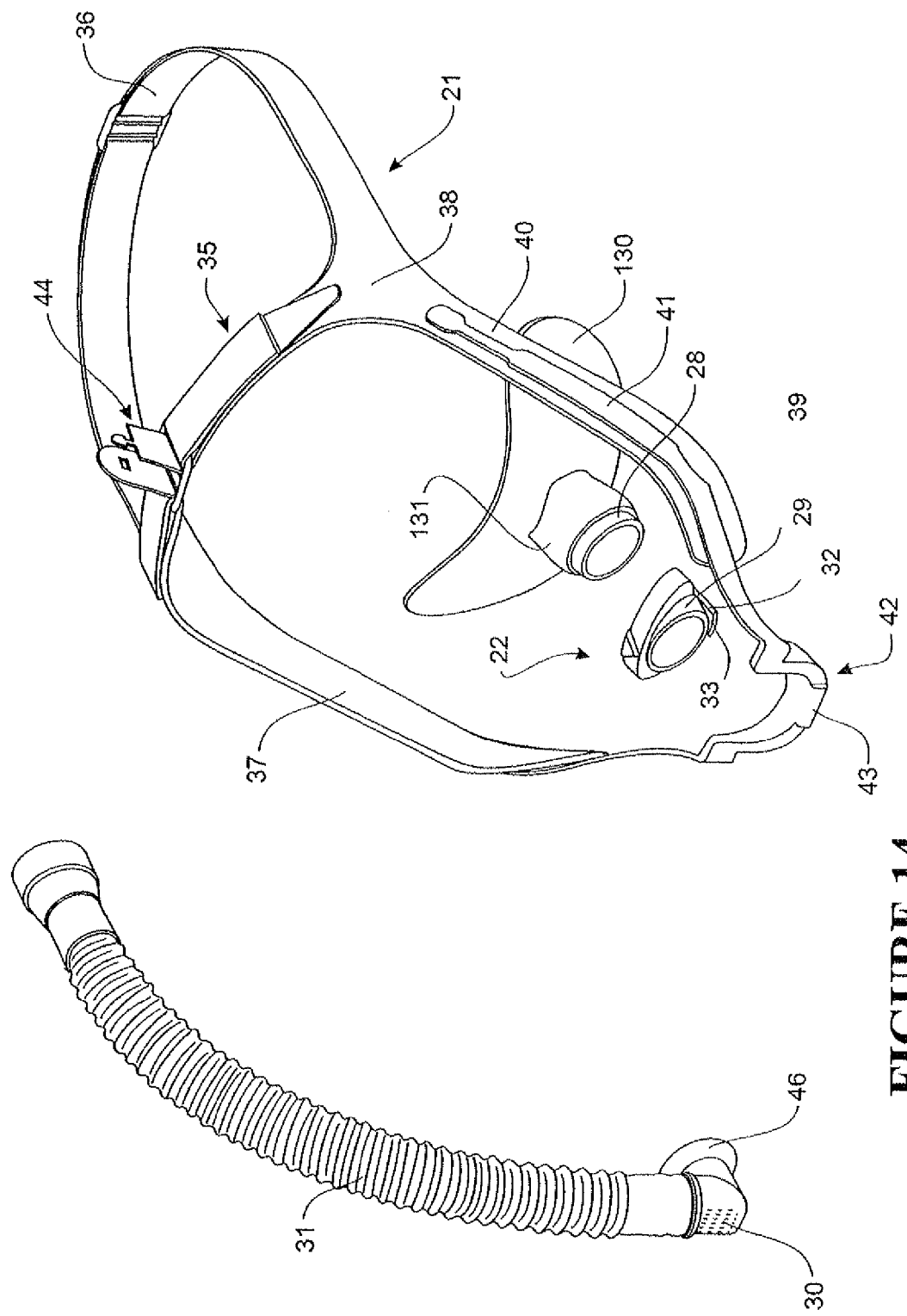
FIG. 14 is an exploded view of the patient interface and headgear of FIG. 13.

A fifth form of the patient interface and headgear of the present invention is shown in FIGS. 13 and 14. This embodiment is very similar to the fourth embodiment except the mouthpiece is simply an outer mouthpiece flap 130. This flap 130 is liftable to the mask base 22 by way of the tubular extension 131. Again, as above, the headgear and particularly the curved member 34 are substantially the same as that described in relation to the first embodiment.

Figure 15:
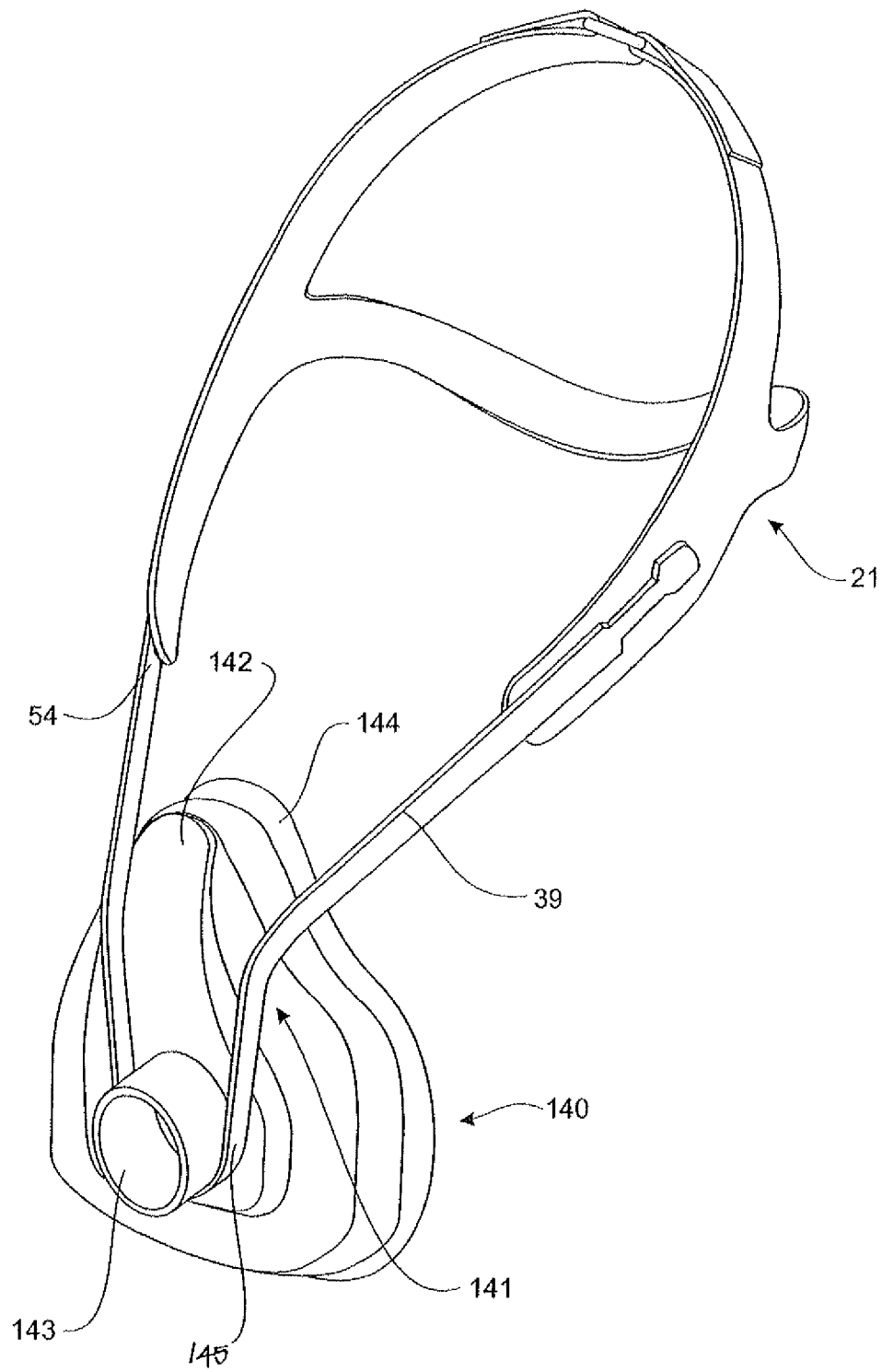
FIG. 15 is a perspective view of a sixth form of a patient interface and headgear of the present invention.

A sixth form of the patient interface and headgear of the present invention is shown in FIG. 15. In this embodiment the patient interface is a full face mask 140 that extends over a user's nose and mouth and under the user's chin in use. The mask 140 has a body 142 made from a substantially rigid plastics material and a cushion 144 made from a substantially soft plastics material. The mask and cushion are preferably similar to that described in more detail in U.S. patent application Ser. No. 11/368,004, the entire contents of which is incorporated herein by reference.

A tubular inlet port 143 is formed in the mask body 142. The tubing 31 is attachable to the port 143 to provide gases to the user wearing the mask.

The headgear is substantially similar to that described in relation to FIG. 2 (the second form); however, the curved member 141 differs. The curved member 141 does not have a mask base similar to that described in the second form in which to attach to. Therefore, the curved member 141 has a central section 145 that curves under the inlet port 143, effectively anchoring on the inlet port. The curved member 141 is moulded in substantially the same manner as described with reference to the second form.

Figure 16:
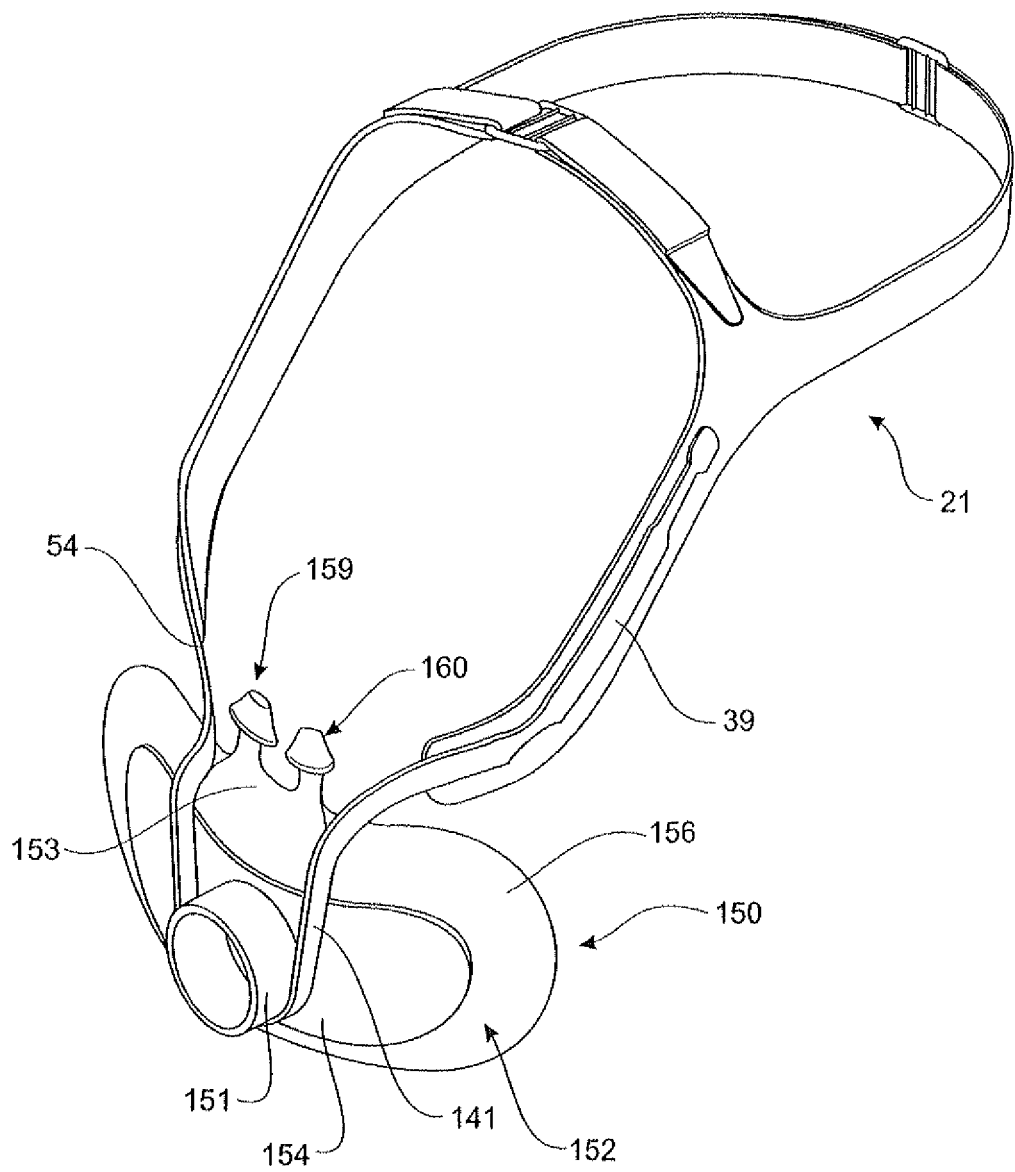
FIG. 16 is a perspective view of a seventh form of a patient interface and headgear of the present invention.
Figure 17:
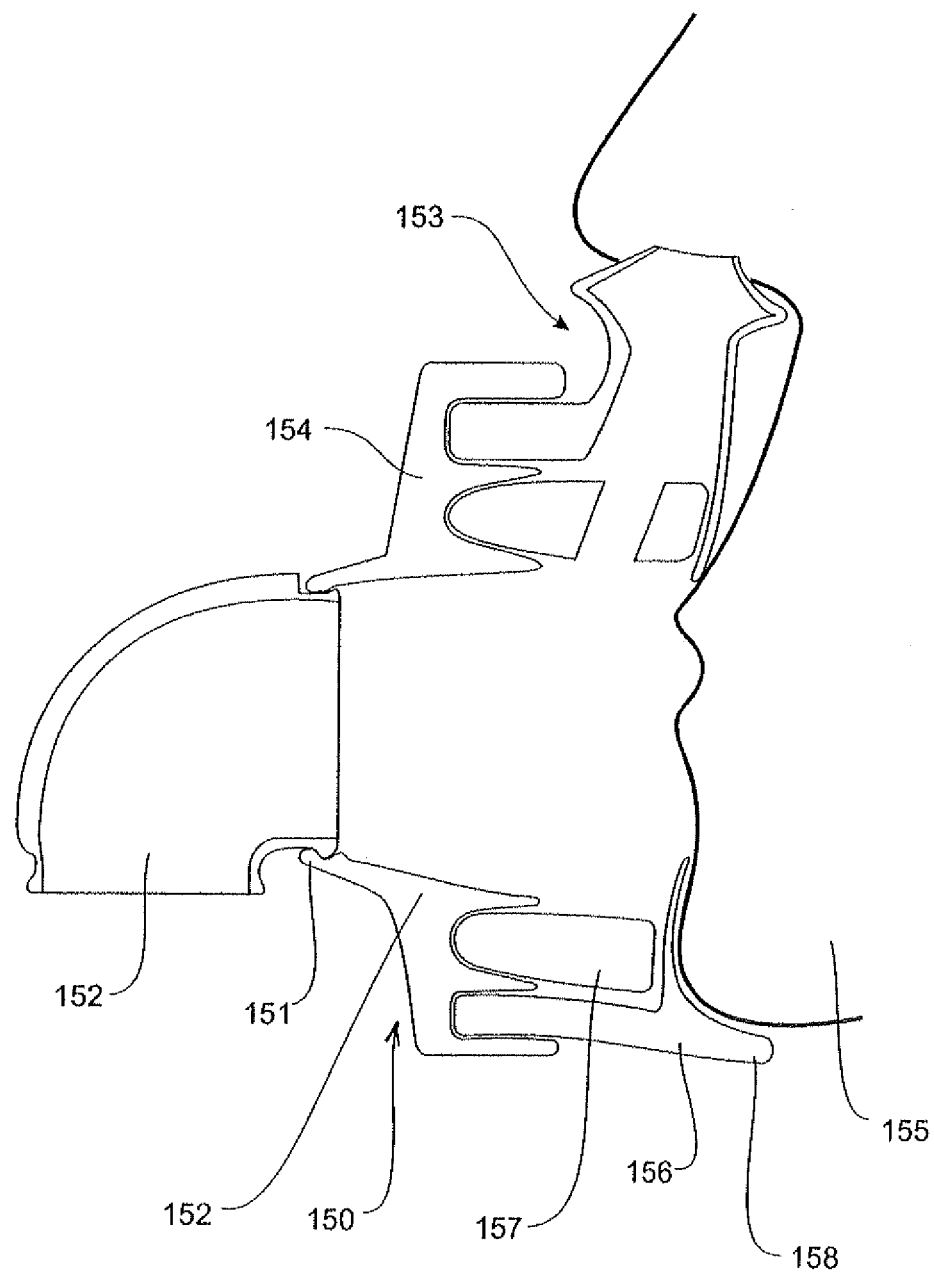
FIG. 17 is a cross-sectional view of the patient interface of FIG. 16.

A seventh form of the patient interface and headgear of the present invention is shown in FIGS. 16 and 17. Here, the headgear and curved member is similar to that described above in the sixth embodiment, where the curved member 141 has a central section that curves under and anchors onto an inlet port 151 on a patient interface 150. The patient interface 150 is an integral mouth mask 152 and nasal pillows 153. The mouth mask 152 preferably extends under the user's 155 chin, as shown in FIG. 17.

The interface 150 has a substantially rigid body 154 that has substantially soft cushion 156 attached to it. The cushion 156 is preferably of the type disclosed in U.S. Pat. No. 6,951, 218 (the entire contents of which is incorporated herein by reference) having an inner 157 and outer 158 cushions.

Integrally formed in the outer cushion 158 are nasal pillows 153. Preferably two nasal pillows 159, 160 are formed in the cushion 158. These are substantially tubular and carry gases in use from the inside of the interface 150 to the user's 155 flares. The outer cushion 158 and nasal pillows 159, 160 are preferably made from a soft pliable plastics material such as silicone but other appropriate materials such as rubber or KRATON™ may be used.

Figure 23:
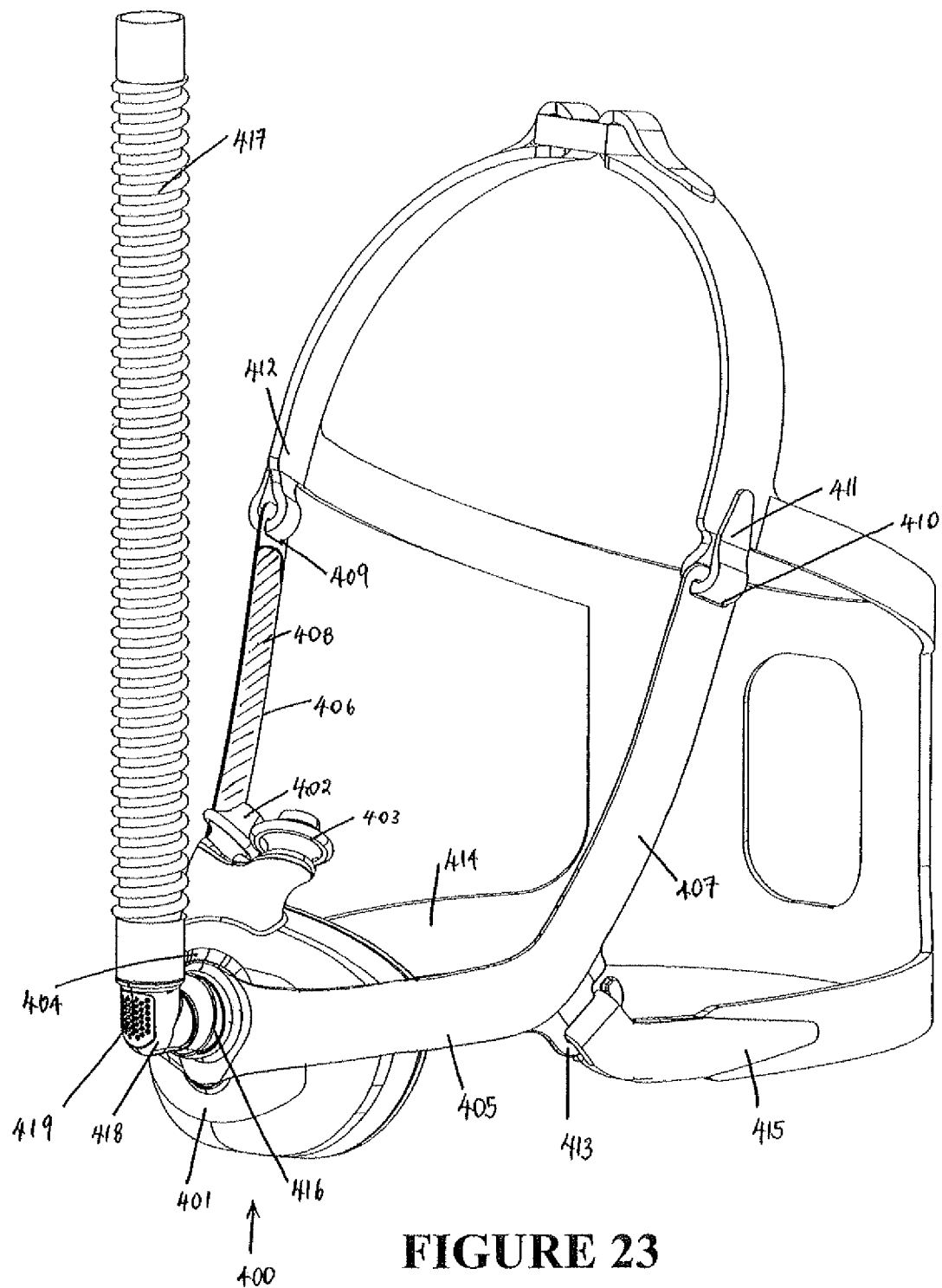
FIG. 23 is a perspective view of a ninth form of a patient interface and headgear the present invention.

A similar but slightly different embodiment to that of FIG. 16 is a ninth embodiment of the present invention, as shown in FIG. 23. Here the interface 400 is substantially the same as the interface 150 of FIGS. 16 and 17. The interface 400 has a body 401 with integral nasal pillows 402, 403. The nasal pillows may be integrally formed with the body or separately formed and simply assembled to the body before use. The nasal pillows 402, 403, as above, are substantially tubular and carry gases in use from the inside of the interface 400 to the user's mires. Again, nasal pillows are preferably made from a soft pliable plastics material such as silicone but other appropriate materials such as rubber or KRATON™ may be used.

In this embodiment the body 401 may be made of a more rigid material than the nasal pillows or simply be made from a soft pliable plastics material as are the nasal pillows.

Attached to an inlet 404 of the body 401 is an elongate member 405 similar to that described in any of the embodiments detailed above, but particularly that of FIGS. 20 to 22. The elongate member 405 has arms 406, 407 that extend along a user's cheekbones then up towards the user's ears when in use. The arms 406, 407 are preferably made from a substantially rigid material, preferably a plastics material. For the users comfort each of the arms 406, 407 have inner pads (only one pad 408 is shown in FIG. 23) extending along their inner sides, particularly where the arms are incident on the user's face.

The arms 406, 407 have recesses 409, 410 at there ends to which headgear straps 411, 412 are attached. The arms 406, 407 may also each have optional side hooks (of which only one side hook 413 is shown), again made out of a substantially rigid material, to which additional side headgear straps 414, 415 may be attached.

At the centre of the elongate member 405 is formed an integral inlet 416 that matches and attaches to the inlet 404 on the body. This integral inlet 416 receives a conduit or tube 417 that is connected in use to a supply of gases. Preferably the tube 417 has a swivelable elbow 418 (for example, a ball joint socket similar to the one described above). Preferably on the elbow 418 are a number of holes 419 that provide an exhaust vent for gases exhaled by the patient in use.

In this ninth embodiment of the patient interface and headgear the interface is a mouth mask and nasal pillows. In alternative forms the patient interface may be a full face mask that is attached to an elongate member and headgear similar in form to those described above and particularly in relation to FIG. 23.

The invention claimed is:

1. A breathing assistance apparatus for use with delivery of respiratory gases to a user comprising:
   a mask comprising a base and a body, said body having two flexible nasal pillows that in use are adapted to rest in a substantially sealed manner against a user's nares, said nasal pillows being substantially elliptical and having gases outlets that are offset from a center of said elliptical pillows said body extending laterally outward and upward beyond said base,
   a continuous and substantially curved elongate member having at least two ends and adapted to extend in use below a user's nose,
   at least two headgear straps capable of attachment to the ends of said elongate member, and
   a mask attachment on said elongate member adapted to be disposed below said user's nose, said attachment capable of receiving said mask.

2. A breathing assistance apparatus according to claim 1 wherein said at least two straps are substantially flexible, soft straps each adapted to extend down a user's cheekbones in use and is adapted to terminate at each of said strap's ends in a user's upper lip area and said a substantial portion of said elongate member is attached to each of said straps.

3. A breathing assistance apparatus according to claim 1 wherein a length of said at least two straps that is adapted to extend in use along a user's cheekbones is attached to said elongate member, said elongate member providing rigidity to said length of said at least two straps.

4. A breathing assistance apparatus according to claim 1 wherein said elongate member has two ends each of which is attached to one of said at least two straps, said elongate member having at least one pad extending along an inner side of the elongate member in at least areas where the elongate member is adapted to be incident on a user's cheekbones.

5. A breathing assistance apparatus according to claim 4 wherein said at least one pad is substantially the same width as said elongate member.

6. A breathing assistance apparatus according to claim 1 wherein said continuous elongate member is substantially rigid compared to said straps.

7. A breathing assistance apparatus according to claim 1 wherein said breathing assistance apparatus includes humidification means adapted to, in use, be in fluid communication with a source of gases and transportation means and adapted to in use humidify said gases.

8. A breathing assistance apparatus according to claim 1 wherein said continuous elongate member includes two side arms and a central section.

9. A breathing assistance apparatus according to claim 8 wherein said side arms and said central section are formed as a single item.

10. A breathing assistance apparatus according to claim 8 wherein said side arms and said central section are formed as two separate items.

11. A breathing assistance apparatus according to claim 4 wherein said continuous elongate member includes two side arms, and wherein said at least one pad is two pads one each extending substantially along a length of each said side arm.

12. A breathing assistance apparatus according to claim 8 wherein said side arms have at least one weakened or narrow area to allow for manipulation of said side arms.

13. A breathing assistance apparatus according to claim 1, wherein said continuous elongate member includes a central section, and wherein said base frictionally fits to said central section, and said body to said base, such that said central section adapted to suspend said base below said user's nares, and when said body is attached to said base, said nasal pillows being adapted to rest against said user's nares.

14. A breathing assistance apparatus according to claim 1, wherein said continuous elongate member includes a central section, and wherein said base is integrally formed with said central section.

15. A breathing assistance apparatus according to claim 1, wherein said continuous elongate member includes at least two side arms, and wherein said side arms attach one to each side of said base.

16. A breathing assistance apparatus according to claim 1 wherein said curved elongate member is moulded in a three dimensional manner and adapted to to fit contours of a user's cheeks.

17. A breathing assistance apparatus according to claim 1 wherein said mask attachment is adapted to be disposed to sit below or on one of a user's nose, mouth, upper lip and an inlet to the mask.

18. A breathing assistance apparatus for use with delivery of respiratory gases to a user comprising:
   a mask having a base and body said body extending laterally outward and upward beyond said base,
   said body having two nasal pillows and an external lip, said nasal pillows in use adapted to rest in a substantially sealed manner against a user's nares,
   said base having a channel, where said external lip on said body fits in use into said channel,
   said external lip having one of a projection or recess that in use fits into one of a corresponding recess or projection on said mask base to ensure correct assembly of said mask.

19. A breathing assistance apparatus for use with delivery of respiratory gases to a user according to claim 18 wherein said external lip is an area of reduced circumference.

20. A breathing assistance apparatus for use with delivery of respiratory gases to a user according to claim 18 wherein said external lip is held in place in use by a bump fit.

21. A breathing assistance apparatus for use with delivery of respiratory gases to a user according to claim 18 wherein said channel has an internal wall extending within the base.

22. A breathing assistance apparatus for use with delivery of respiratory gases to a user according to claim 18 wherein said body and said nasal pillows are integrally formed.

23. A breathing assistance apparatus for use with delivery of respiratory gases to a user comprising:
    a mask having a base and body, said body having two nasal pillows that in use are adapted to rest in a substantially sealed manner against a user's naressaid body extending laterally outward and upward beyond said base,
    two arms extending from either side of said base of said mask and adapted to be disposed along a user's cheekbones, said two arms where one of said two headgear straps is attachable to one of said two arms and another of said two headgear straps is attachable to another of said two arms being moulded to a shape that substantially matches cheek contours of a human, and
    at least two headgear straps capable of attachment to one each of said two arms where one of said two headgear straps is attachable to one of said two arms and another of said two headgear straps is attachable to another of said two arms.

24. A breathing assistance apparatus for use with delivery of respiratory gases to a user according to claim 23 wherein said two arms are three dimensionally moulded.

25. A breathing assistance apparatus for use with delivery of respiratory gases to a user according to claim 23 wherein one of said at least two headgear straps extends in use over a user's head and has an attachment capable of receiving and locating tubing to said one of said at least two headgear straps.

26. A breathing assistance apparatus for use with delivery of respiratory gases to a user according to claim 23 wherein said body and said nasal pillows are integrally formed, wherein a tubing and an elbow connector are capable of attachment to said mask so as to deliver gases to said mask, and wherein one of said at least two headgear straps is adapted to extend in use over a user's head and has an attachment capable of receiving and locating said tubing to said one of said at least two headgear straps.

27. A breathing assistance apparatus for use with delivery of respiratory gases to a user according to claim 26 wherein said base has a socket that receives said elbow connector and allows said elbow connector to rotate.

28. A breathing assistance apparatus for use with delivery of respiratory gases to a user according to claim 26 wherein said elbow connector has a plurality of holes that are adapted to exhaust gases exhaled by said user in use.

29. A breathing assistance apparatus for use with delivery of respiratory gases to a user according to claim 23 wherein said body has an external lip and said base has a channel, where said external lip on said body fits in use into said channel.

30. A breathing assistance apparatus for use with delivery of respiratory gases to a user comprising:
    a mask having a base and body, said body having two nasal pillows that in use are adapted to rest in a substantially sealed manner against a user's nares said body extending laterally outward and upward beyond said base,
    two arms extending from either side of said base and adapted to be disposed base along a user's cheekbones, said two arms having a varying cross-sectional thickness, and
    at least two headgear straps capable of attachment to one each of said two arms where one of said two headgear straps is attachable to one of said two arms and another of said two headgear straps is attachable to another of said two .

31. A breathing assistance apparatus for use with delivery of respiratory gases to a user according to claim 30 wherein said two arms are more curved at their ends where they attach to said mask base and have straighter parts that are adapted to extend over regions of the user's cheekbones.

32. A breathing assistance apparatus for use with delivery of respiratory gases to a user according to claim 31 wherein said more curved ends are thicker in cross-section.

33. A breathing assistance apparatus for use with delivery of respiratory gases to a user according to claim 31 wherein said two arms are each thin in cross-section along said straighter parts in order to allow for bending or adjusting of said two arms.

34. A breathing assistance apparatus for use with delivery of respiratory gases to a user according to claim 30 wherein said two arms each have narrow areas that are adapted to be in a region of a user's cheekbone.

35. A breathing assistance apparatus for use with delivery of respiratory gases to a user comprising:
    a mask having a base and body, said body extending laterally outward and upward beyond said base,
    a continuous and substantially curved elongate member having at least two ends and adapted to extend in use below a user's nose,
    at least two headgear straps capable of attachment to the ends of said elongate member, and
    a mask attachment on said elongate member adapted to be disposed below said user's nose, said attachment capable of receiving said mask wherein said elongate member has two ends each of which is attached to one of said at least two straps, said elongate member having at least one pad extending along an inner side of the elongate member in at least the areas where the elongate member is incident adapted to be on a user's cheekbones, wherein said elongate member includes two side arms, and wherein said at least one pad is two pads one each extending substantially along a length of each said side arm.

36. A breathing assistance apparatus according to claim 35 wherein said mask comprises a base and body, said body having two flexible nasal pillows that are adapted to in use rest in a substantially sealed manner against the user's nares.

37. A breathing assistance apparatus according to claim 35 wherein said at least two straps are substantially flexible, soft straps each is adapted to extend down said user's cheekbones in use and adapted to terminate at each of said strap's ends in a user's upper lip area and said a substantial portion of said elongate member is attached to each of said straps.

38. A breathing assistance apparatus according to claim 35 wherein a length of said at least two straps that is adapted to extend in use along said user's cheekbones is attached to said elongate member, said elongate member providing rigidity to said length of said at least two straps.

39. A breathing assistance apparatus according to claim 35 wherein said at least one pad is substantially the same width as said elongate member.

40. A breathing assistance apparatus according to claim 35 wherein said continuous elongate member is substantially rigid compared to said straps.

41. A breathing assistance apparatus according to claim 36 wherein said nasal pillows are substantially elliptical and have gases outlets that are offset from the center of said elliptical pillows.

42. A breathing assistance apparatus according to claim 35 wherein said breathing assistance apparatus includes humidification means adapted to, in use, be in fluid communication with a source of gases and transportation means and adapted to in use humidify said gases.

43. A breathing assistance apparatus according to claim 35 wherein said continuous elongate member includes two side arms and a central section.

44. A breathing assistance apparatus according to claim 43 wherein said side arms and said central section are formed as a single item.

45. A breathing assistance apparatus according to claim 43 wherein said side arms and said central section are formed as two separate items.

46. A breathing assistance apparatus according to claim 43 wherein said side arms have at least one weakened or narrow area to allow for manipulation of said side arms.

47. A breathing assistance apparatus according to claim 36 wherein said continuous elongate member includes a central section, and wherein said base frictionally fits to said central section, and said body to said base, such that said central section is adapted to suspend said base below said user's nares, and when said body is attached to said base, said nasal pillows being adapted to rest against said user's nares.

48. A breathing assistance apparatus according to claim 36 wherein said continuous elongate member includes a central section, and wherein said base is integrally formed with said central section.

49. A breathing assistance apparatus according to claim 36 wherein said side arms attach one to each to each side of said base.

50. A breathing assistance apparatus according to claim 35 wherein said curved elongate member is moulded in a three dimensional manner and adapted to fit contours of a user's cheeks.

51. A breathing assistance apparatus according to claim 36 wherein said mask attachment is adapted to sit below or on one of a user's nose, mouth, upper lip and an inlet to the mask.

52. A breathing assistance apparatus for use with delivery of respiratory gases to a user comprising:
a mask having a base and body, said body extending laterally outward and upward beyond said base,
a continuous and substantially curved elongate member having at least two ends and adapted to extend in use below a user's nose, said elongate member including two side arms and a central section, said side arms having at least one weakened or narrow area to allow for manipulation of said arms,
at least two headgear straps capable of attachment to the ends of said elongate member, and
a mask attachment on said elongate member adapted to be disposed below said user's nose, said attachment capable of receiving said mask.

53. A breathing assistance apparatus according to claim 52 wherein said at least two straps are substantially flexible, soft straps each adapted to extend down a user's cheekbones in use and is adapted to terminate at each of said strap's ends in said a user's upper lip area and said a substantial portion of said elongate member is attached to each of said straps.

54. A breathing assistance apparatus according to claim 52 wherein a length of said at least two straps that is adapted to extend in use along said a user's cheekbones is attached to said elongate member, said elongate member providing rigidity to said length of said at least two straps.

55. A breathing assistance apparatus according to claim 52 wherein said elongate member has two ends each of which is attached to one of said at least two straps, said elongate member having at least one pad extending along an inner side of the elongate member in at least areas where the elongate member is adapted to be incident on a user's cheekbones.

56. A breathing assistance apparatus according to claim 55 wherein said at least one pad is substantially the same width as said elongate member.

57. A breathing assistance apparatus according to claim 52 wherein said continuous elongate member is substantially rigid compared to said straps.

58. A breathing assistance apparatus according to claim 52 wherein said mask comprises a base and body, said body having two flexible nasal pillows that in use are adapted to rest in a substantially sealed manner against a user's nares.

59. A breathing assistance apparatus according to claim 52 wherein said breathing assistance apparatus includes humidification means adapted to, in use, be in fluid communication with a source of gases and transportation means and adapted to in use humidify said gases.

60. A breathing assistance apparatus according to claim 52 wherein said side arms and said central section are formed as a single item.

61. A breathing assistance apparatus according to claim 52 wherein said side arms and said central section are formed as two separate items.

62. A breathing assistance apparatus according to claim 55 wherein said at least one pad is two pads one each extending substantially along a length of each said side arm.

63. A breathing assistance apparatus according to claim 58, wherein said continuous elongate member includes a central section, and wherein said base frictionally fits to said central section, and said body to said base, such that said central section is adapted to suspend said base below said user's nares, and when said body is attached to said base, said nasal pillows being adapted to rest against said user's nares.

64. A breathing assistance apparatus according to claim 58, wherein said continuous elongate member includes a central section, and wherein said base is integrally formed with said central section.

65. A breathing assistance apparatus according to claim 58, wherein said continuous elongate member includes at least two side arms, and wherein said side arms attach one to each side of said base.

66. A breathing assistance apparatus according to claim 52 wherein said curved elongate member is moulded in a three dimensional manner and adapted to fit contours of a user's cheeks.

67. A breathing assistance apparatus according to claim 58 wherein said nasal pillows are substantially elliptical and have gases outlets that are offset from the center of said elliptical pillows.

68. A breathing assistance apparatus according to claim 58 wherein said mask attachment is adapted to be disposed to sit below or on one of a user's nose, mouth, upper lip and an inlet to the mask.

* * * * *

UNITED STATES PATENT AND TRADEMARK OFFICE
CERTIFICATE OF CORRECTION

| | |
|---|---|
| PATENT NO. | : 9,138,555 B2 |
| APPLICATION NO. | : 12/633135 |
| DATED | : September 22, 2015 |
| INVENTOR(S) | : Alastair Edwin McAuley |

It is certified that error appears in the above-identified patent and that said Letters Patent is hereby corrected as shown below:

In The Specification

In column 2 at line 21, Change "that;" to --that,--.

In column 2 at line 42, Change "flares" to --nares--.

In column 4 at line 6, Change "6," to --6.--.

In column 5 at line 35, Change "24," to --24, 25--.

In column 6 at line 53, Change "semicircular" to --semi-circular--.

In column 7 at line 8, Change "checks" to --cheeks--.

In column 7 at line 17, Change "soil" to --soft--.

In column 8 at line 18, Change "311,312" to --311, 312--.

In column 8 at line 24, Change "303,304." to --303, 304.--.

In column 10 at line 5, Change "liftable" to --fittable--.

In column 10 at line 49, Change "flares." to --nares.--.

In column 10 at line 62, Change "mires." to --nares.--.

In column 11 at line 12, Change "there" to --their--.

In The Claims

In column 11 at line 41, In Claim 1, change "pillows" to --pillows,--.

In column 12 at line 46, In Claim 16, after "adapted" delete "to".

In column 12 at line 54, In Claim 18, change "body" to --body,--. (First Occurrence)

In column 13 at line 14, In Claim 23, change "naressaid" to --nares, said--.

In column 13 at line 62, In Claim 30, change "nares" to --nares,--.

In column 14 at line 5, In Claim 30, change "two ." to --two arms.--.

In column 14 at line 41, In Claim 35, change "incident adapted to be" to --adapted to be incident--.

In column 15 at line 34, In Claim 49, change "to each to each" to --to each--.

Signed and Sealed this
Fourteenth Day of June, 2016

Michelle K. Lee
*Director of the United States Patent and Trademark Office*